United States Patent
Garcia Morchon et al.

(10) Patent No.: US 9,094,383 B2
(45) Date of Patent: Jul. 28, 2015

(54) PERSONAL SECURITY MANAGER FOR UBIQUITOUS PATIENT MONITORING

(75) Inventors: Oscar Garcia Morchon, Aachen (DE); Axel Guenther Huebner, Munich (DE); Heribert Baldus, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 830 days.

(21) Appl. No.: 12/995,677

(22) PCT Filed: Jun. 10, 2009

(86) PCT No.: PCT/IB2009/052471
§ 371 (c)(1),
(2), (4) Date: Dec. 2, 2010

(87) PCT Pub. No.: WO2009/153710
PCT Pub. Date: Dec. 23, 2009

(65) Prior Publication Data
US 2011/0145894 A1  Jun. 16, 2011

(30) Foreign Application Priority Data
Jun. 18, 2008 (EP) .................................... 08104451

(51) Int. Cl.
*H04L 29/06* (2006.01)
*G06F 19/00* (2011.01)
(Continued)

(52) U.S. Cl.
CPC ............ *H04L 63/062* (2013.01); *A61B 5/0022* (2013.01); *A61B 5/0024* (2013.01);
(Continued)

(58) Field of Classification Search
CPC ................................ G06F 21/00; G01R 11/24
USPC ...................................... 726/4, 5, 6, 7, 26, 27
See application file for complete search history.

(56) References Cited

U.S. PATENT DOCUMENTS 6,564,056 B1    5/2003  Fitzgerald
6,616,607 B2 *  9/2003  Hashimoto et al. ........... 600/300
(Continued)

FOREIGN PATENT DOCUMENTS

DE   20008602 U1    9/2000
WO   2007149850 A2  12/2007
(Continued)

OTHER PUBLICATIONS

Blundo et al, "Perfectly-Secure Key Distribution for Dynamic Conferences" Advances in Cryptology, CRYPTO 92, Springer-Verlag, Berlin, 1993, pp. 471-486.*
(Continued)

*Primary Examiner* — Tamara T Kyle

(57) ABSTRACT

The present invention relates to a system and corresponding method for a secure end-to-end patient healthcare system which includes wireless medical sensors adapted to be attached to a patient's body and in communication with each other forming a body sensor network within a wireless medical sensor network including one or more body sensor networks; λ-secure keying means incorporated into each wireless medical sensor for enabling secure communications between the wireless medical sensors, and a personal security manager within the body sensor network and in communication with the wireless medical sensors within the body sensor network, the personal security manager providing secure communications with backend services and providing security relationships within the body sensor network by means of the λ-secure keying means, wherein the λ-secure keying means are such that a coalition of no more than λ compromised wireless medical sensors conceals a pairwise key between any two non-compromised wireless medical sensors and provides protection against node compromise until λ+1 wireless medical sensors have been compromised.

13 Claims, 12 Drawing Sheets

(51) Int. Cl.
*G06F 21/62* (2013.01)
*H04W 12/04* (2009.01)
*H04L 9/08* (2006.01)
*H04L 9/32* (2006.01)
*H04L 29/08* (2006.01)
*A61B 5/00* (2006.01)

(52) U.S. Cl.
CPC ........ *G06F19/3412* (2013.01); *G06F 19/3418* (2013.01); *G06F 21/6245* (2013.01); *H04L 9/0844* (2013.01); *H04L 9/3263* (2013.01); *H04L 9/3273* (2013.01); *H04L 67/125* (2013.01); *H04W 12/04* (2013.01); *H04L 2209/805* (2013.01); *H04L 2209/88* (2013.01)

(56) References Cited

U.S. PATENT DOCUMENTS

| | | | | |
|---|---|---|---|---|
| 7,234,063 | B1* | 6/2007 | Baugher et al. | 713/189 |
| 2002/0188473 | A1 | 12/2002 | Jackson | |
| 2003/0229518 | A1 | 12/2003 | Abraham-Fuchs et al. | |
| 2004/0167465 | A1* | 8/2004 | Mihai et al. | 604/67 |
| 2004/0199056 | A1* | 10/2004 | Husemann et al. | 600/300 |
| 2004/0268119 | A1* | 12/2004 | Smetters et al. | 713/155 |
| 2005/0130634 | A1* | 6/2005 | Godfrey | 455/414.1 |
| 2005/0135305 | A1* | 6/2005 | Wentink | 370/329 |
| 2005/0204134 | A1 | 9/2005 | Von Arx et al. | |
| 2005/0245995 | A1 | 11/2005 | Diebold | |
| 2006/0224048 | A1* | 10/2006 | Devaul et al. | 600/300 |
| 2007/0043594 | A1 | 2/2007 | Lavergne | |
| 2008/0129465 | A1 | 6/2008 | Rao | |

FOREIGN PATENT DOCUMENTS

| | | |
|---|---|---|
| WO | 2008014432 A2 | 1/2008 |
| WO | 2008021920 A2 | 2/2008 |

OTHER PUBLICATIONS

Baldus et al: "Reliable Set-Up of Medical Body-Sensor Networks"; H. Karl, A. Willig, A. Wolisz (Eds.) EWSN 2004, LNCS 2920, pp. 353-363.

Andersen et al: "BLIG:A New Approach for Sensor Identification, Grouping, and Authorisation in Body Sensor Networks"; 4th International Workshop on Wearable and Implantable Body Sensor Networks, (BSN 2007), pp. 223-229.

Falck et al: "Plug 'N. Play Simplicity for Wireless Medical Body Sensors"; Pervasive Health Conference and Workshops, 2006, 5 Page Document.

Anderson, R.: "A Security Policy Model for Clinical Information Systems"; 1996 IEEE Symposium on Security and Privacy, pp. 30-43.

Sohr et al: "Formal Specification of Role-Based Security Policies for Clinical Information Systems"; 2005 ACM Symposium on Applied Computing, (SAC'05), pp. 332-339.

Garcia Morchon et al: "Hierarchical Key Pre-Distribution for Mobile Sensor Networks"; Philips Research Laboratories, 6 Page Document.

* cited by examiner

|  | | Time (MSEC) | RAM (BYTES) | ROM (BYTES) | KEYING MATE-RIAL (BYTES) |
|---|---|---|---|---|---|
| MICAz | RSA-1024 (PUBLIC KEY) | 430 | 542 | 1,073 | 128 |
| | RSA-1024 (PRIVATE KEY) | 10,990 | 930 | 6,292 | 128 |
| | ECC SECP 160 R1 | 810 | 282 | 3,682 | 20 |
| | DISTRIBUTED KEY AGREEMENT | $0.0625 \cdot \lambda$ | 20 | 416 | $8 \cdot \lambda$ |
| UPD789828 | SHA 512 BITS | 2 | - | - | 64 |
| | ECDSA 255 SIGN | 81 | - | - | 32 |
| | ECDSA 255 | 380 | - | - | 32 |

FIG. 13

|  | MEMORY Kbytes | $N_{IJ}$ | $\alpha$ | $\alpha_r$ |
|---|---|---|---|---|
| $SD_{MSN}$ | 800 | 1,000 | 100 | 0.1 |
| $SD_{HOSPITAL}$ | 408 | 500 | 51 | 0.102 |
| $SD_{DEPARTM.}$ | 224 | 100 | 28 | 0.28 |
| $SD_{OZ}$ | 308 | 100 | 38.5 | 0.385 |
| $SD_{MED.SPEZ}$ | 308 | 125 | 38.5 | 0.308 |
| $M\lambda KE$ | 2,048 | - | 385 | 0.385 |

FIG. 14

PERSONAL SECURITY MANAGER FOR UBIQUITOUS PATIENT MONITORING

FIELD OF THE INVENTION

The present invention relates to electronic security systems. More particularly, the invention relates to an apparatus and a corresponding method for secure healthcare access and monitoring.

BACKGROUND OF THE INVENTION

Wireless sensor networks are increasingly deployed for health monitoring, leading to ubiquitous patient monitoring systems. In these systems, each patient carries a body sensor network (BSN) that enables the monitoring of his vital signs at home, at hospitals, or virtually anywhere. In this context, a patient can be monitored in very different scenarios and with different sets of medical sensor nodes or devices.

Sensor and wireless communication technologies are rapidly evolving and conquering new application areas, such as healthcare. Wireless medical sensors (WMSs) are becoming smaller and more powerful, allowing for ubiquitous usage for a wide range of medical applications, such as chronic disease management. In a typical healthcare setting, a set of WMSs which provide measurements of a variety of parameters, e.g., ECG, $SpO_2$ and blood pressure, forms the user's body sensor network (BSN), allowing for health monitoring, measuring a user's vital signs and forwarding his electronic health information (EHI) to a gateway, such as a mobile phone. The gateway allows the user to directly access and process his EHI, and moreover, transmits it, e.g., to a healthcare service provider, where it is stored and can be accessed or modified by authorized parties, such as medical staff, family, or sport trainers.

The ubiquitous use of BSNs enables health monitoring in users' regular environments, e.g., at home or during training, and thus, improves users' well-being and healthcare quality, yet allows for cost reduction in the healthcare sector. Health monitoring in these diverse situations and locations is carried out by different organizations, such as surgeries, fitness centers, hospitals, or retirement homes by means of medical sensor networks (MSNs). An MSN comprises a large pool of WMSs used to monitor vital signs of a few or many users with disease-specific sensors and algorithms. Thus, MSNs have different operational requirements with respect to their size, capabilities, or field of application. In an MSN, an arbitrary subset of WMSs can be associated with a patient to form his BSN and monitor his state of health in real-time. The user's measured EHI can be processed by the WMSs of the BSN or by a clinical PDA, or can be sent via a gateway to either a local MSN database or back-end healthcare services, e.g., the healthcare service provider, disease management service, personal health record service or the implant monitoring service, for further processing.

Pervasive MSNs are decoupled from each other as they may belong to different organizations. Consequently, WMSs that are from different MSNs might not be interoperable on the hardware and software levels due to technical incompatibilities, or on the organizational level due to different security policies. However, the vision of pervasive healthcare requires all MSN application scenarios to work together and to be connected to back-end services in order to allow users to move across MSNs and to ensure that their health state can be monitored by authorized personnel of different organizations, including hospitals or insurance companies.

The exchange of users' medical data intra- and inter-MSNs leads to privacy and security concerns demanding basic security services, e.g., confidentiality and authentication. These security services must ensure patients' safety and privacy, as required by healthcare alliances such as HITRUST, and must comply with legal directives such as the Health Insurance Portability and Accountability Act (HIPAA) in the United States and the European directive 95/46 on data protection. In particular, a users' EHI must be protected from end-to-end, that is, from his BSN's WMSs to MSN databases and back-end healthcare services in order to prevent unauthorized parties from accessing their medical data. However, providing privacy in such an environment is challenging due to MSNs features including: (i) inter- and intra-MSNs user mobility; (ii) the resource-constrained nature of WMSs; (iii) the fact that any subset of WMSs of an MSN's WMS pool can form the BSN used to monitor the health state of a user; (iv) and the requirement of unambiguous user and BSN identification in the whole system of pervasive MSNs.

Security and privacy issues have been addressed for both the centralized back-end services and isolated MSN application scenarios. For instance, an XML security infrastructure was introduced to provide access control to EHI in the back-end infrastructure. Security issues for wireless sensor networks in isolated healthcare applications were analyzed. Security requirements and infrastructure for stand-alone clinical information systems have been presented. However, the state-of-the-art lacks the definition of a comprehensive security system where a patient's BSN can be unambiguously identified in the whole system of pervasive MSNs, where WMSs can be associated to a patient's patient area network (PAN) or BSN in a secure and efficient manner, and where end-to-end security can be provided by means of an efficient key distribution approach.

It is a challenge to meet the strict security requirements for medical applications which are legally required by directives such as HIPAA. The safety and privacy of a user's medical data must be ensured from end-to-end, i.e., from the individual sensor nodes to the back-end healthcare services. This is particular challenging due to the features of pervasive medical sensor networks (MSNs) such as: (i) supporting patient intra- and inter-MSN mobility; (ii) taking into account the resource-constrained nature of medical sensors; (iii) forming a user's body sensor network from any subset of a medical sensor network's pool of wireless medical sensors; and (iv) providing unambiguous user and body sensor network identification.

A pervasive healthcare system is applicable to a broad range of healthcare scenarios and combines diverse technologies. On the organizational level, the pervasive healthcare system may be divided into MSNs controlled by different institutions, e.g., hospitals, fitness centers, surgery centers, or home-based. In general, MSNs are distributed, large-scale, ad hoc networks that operate in a stand-alone fashion. MSNs may comprise a large number of WMSs associated with different patients and BSNs. In general, only WMSs associated with the same patient communicate with each other, so that BSNs are disconnected. Both patient and node mobility makes the MSN topology highly dynamic. In the prior art, on the implementation level, WMSs used in different MSNs are not interoperable, and from a technical and security point view as they might not be based on compatible technologies and may belong to different security domains.

In order to make WMSs wearable and to prevent them from burdening a user's daily life, WMSs need to be small and lightweight. As a result of these size and weight constraints, WMSs are also constrained regarding battery lifetime, available memory, and computational power. In this context, IEEE 802.15.4 and ZigBee are two key standards due to their low energy, memory, and computational requirements, fitting low rate wireless personal area network (PAN) or BSN applications.

Due to the restricted radio range of the WMSs which form a BSN, the WMSs need to rely on a gateway device to ensure persistent connectivity to remote back-end healthcare services that manage, store and give access to the patient's medical data. Communication between gateways and healthcare services may be achieved by wireless means for mobile BSNs, or wired means for applications in a restricted, closed environment, e.g., a hospital. Well known technologies such as WLAN, GSM, UMTS or Ethernet are used for these purposes. The back-end healthcare services may be of a centralized nature, e.g., the healthcare provider service, the personal healthcare record service, or the healthcare security service. However, these healthcare services might also be distributed among various healthcare institutions or insurance companies.

The technical features of the WMSs used in medical applications as well as the operational requirements of MSNs impose novel challenges to the definition of a security system, especially when compared with traditional computer networks or static stand-alone wireless sensor networks.

Firstly, WMSs are resource constrained devices. For instance, the MICAz platform has been used by many research institutions in the design of WMSs. MICAz is outfitted with a program flash memory of 128 Kbytes, a RAM of 4 Kbytes. The radio chip, the CC2420, implements AES in hardware and communicates at 250 kbps, The CPU runs at a clock frequency of 8 MHz and lacks division operation. Therefore, security solutions must be energy-efficient, minimize memory requirements, especially RAM, and consume a negligible amount of computational and communication resources to avoid DoS (Denial of Service) attacks.

Another aspect imposing requirements on medical applications concerns the maximum allowed latency on the transmission of medical information as well as BSN setup time. For instance, ECG requires a maximum latency of 250 msec, and network setup must be carried out in less than 1 second. Therefore, execution time of security procedures must be minimized in order to not restrict everyday's normal operation, e.g., during the ward rounds of a doctor, and to prevent attackers from launching DoS attacks.

Additionally, the security system must be scalable at both the MSNs and the WSN level. On the one hand, the pervasive healthcare architecture must enable adding and integrating new MSNs, e.g., in a new retirement home, in the pervasive healthcare system. On the other hand, a stand-alone MSN can comprise thousands of WMSs, e.g., in a hospital. Hence, security services, as well as their provisioning, must be scalable on both of these levels to enable a truly ubiquitous and secure healthcare system for large numbers of MSNs and patients.

Mobility of WMSs with and between users of an MSN imposes additional requirements on the BSN association and configuration as well as on the key distribution approaches. Firstly, BSN association, which can take place very frequently, must be unobtrusive, automatic, palpable, secure, and transparent for the medical staff, to avoid distraction from patient care. Each BSN can be considered as a dynamic independent security domain within an MSN where WMSs can join and leave at any time, e.g., a new WMS of a hospital's MSN may be attached to a patient, and associated with his BSN. On the other hand, mobility of patients and caregivers makes an MSNs topology dynamic and leads to network segmentation and network mergers. For instance, patients' BSNs in a hospital setting may be disconnected from the hospital's MSN and infrastructure, e.g., when taking a walk in the hospital's garden. Situations such as medical emergencies may require immediate treatment by a doctor. Thus, any doctor must be able to establish secure communication in an ad hoc manner and to monitor the patient's vital signs in a secure manner keeping from using some key-distribution protocols.

Finally, the healthcare system should allow for unique identification of users and BSNs in different MSNs in order to unambiguously link users' EHI which may be generated in different MSNs by different WMSs.

Security Challenges

There are three main security challenges that need to be addressed to define a comprehensive security system: key distribution in pervasive MSNs, secure BSN association, and unambiguous and unique user identification.

KEY DISTRIBUTION is the security cornerstone of both stand-alone MSNs and interconnected MSNs, as this defines how WMSs receive and handle the cryptographic keys used to enable the most basic security requirements, such as confidentiality and authentication both intra- and inter-MSNs. There are a variety of very different key distribution techniques based on public key, centralized (online) trust centers or key sharing. In general, the feasibility of one approach or another depends on the operational requirements and technical restrictions of each specific medical setting. For instance, symmetric cryptographic keys can be preconfigured on the WMSs belonging to a static BSN in a small MSN. However, this configuration is impossible in highly dynamic environments, e.g., hospitals, due to node mobility, where BSN membership is unpredictable. Performing computationally complex operations increases battery drain and communications delay and may render communication protocols susceptible to DoS attacks that could possibly block required processing of medical data. The most efficient implementations of public-key systems based on elliptic curve cryptography still require 0.81 sec. for a single point multiplication, i.e., the basic operation for establishing a common key. This fact makes these key establishment protocols prone to resource exhaustion attacks targeting computational and energy resources. Thus, the use of public key cryptography in MSNs should be minimized as far as possible. Key establishment based on an online trust center (TC) relies on the TC to distribute keys to WMSs, e.g., ZigBee. This approach features the single point of failure nature of the TC and the increased traffic load for nodes on the path to the TC that drains these nodes' batteries. DoS attacks and packet collisions might also prevent WMSs from succeeding in the initial key agreement handshake, and thus, keeping them from transmitting medical data. Additionally, connectivity to a TC cannot be guaranteed in many situations, such as medical emergencies and disaster response. For these reasons, computationally inexpensive symmetric key cryptography solutions that enable direct key agreement, such as hash functions or polynomials, are the preferable option in stand-alone MSNs.

SECURE BSN ASSOCIATION refers to the formation of a BSN and how the WMSs of a BSN are identified and associated with a particular user. In static scenarios, in which only fixed sets of wireless sensors are communicating, the BSN association is carried out only once by means of a simple pairing procedure. However, in more complex settings, such as in retirement homes or hospitals, where a user's BSN may consist of arbitrary sets of WMSs taken from the MSN's WMS pool, WMSs must be associated in a secure manner to a patient. Within the security domain of an MSN, a BSN must be understood as a completely independent security sub-domain wherein the security relationships are handled in an autonomous manner.

The problem of BSN association has recently been addressed in different ways. Baldus et al., "*Reliable Set-Up of Medical Body-Sensor Networks*", EWSN 2004, used a setup pen to distribute the BSN identifier to medical nodes via infrared. The BLIG approach (J. Andersen, and J. E. Bardram. "*BLIG: A New Approach for Sensor Identification, Grouping and Authorization in Body Sensor Networks*". 4th Int. Workshop on Wearable and Implantable Body Sensor Networks, (BSN 2007), Mar. 26-28, 2007, Aachen, Germany.) makes use of a special node attached to the body. The other nodes receive the user identifier when they are brought close to it by means of a short-range communication technology. Falck et al. "*Plug 'n Play Simplicity for Wireless Medical Body Sensors*," Pervasive Health Conference and Workshops, 2006, vol., no., pp. 1-5, Nov. 29 2006-Dec. 1 2006, propose the use of body-coupled communication (BCC) technology to distribute the user and BSN ID. In this approach, each patient carries an identification token that automatically distributes the patient's ID, and other configuration information, to WMSs attached to the patient's body by means of BCC. Therefore, this approach does not require clinician intervention during the BSN setup. However, secure BSN association protocols are needed as these approaches do not support basic security services nor do they allow for transforming a BSN into an independent security domain.

Unambiguous and unique user identification refers to the fact that an individual can be attended in different MSNs with different medical equipment as described previously. Measured medical information must be linked in an automatic manner to a master patient identifier recognized in the whole healthcare system in order to enable interoperability between independent pervasive MSNs. These identifiers should be regulated in order to ensure interoperability between different administrative and healthcare institutions. Dynamic session identifiers might be used to ensure patient's privacy and to identify a patient in a different way depending on the context.

An integrated solution for all three of the requirements described above enables the deployment of secure BSNs and MSNs as well as end-to-end security between WMSs and back-end healthcare services. The design of such a system is challenging and complex, as users might move across different MSN organizations and in some applications users' BSNs can comprise sub-sets of WMSs arbitrarily picked up from the MSN's pool of WMSs.

Additional Security Requirements

In addition to the main security issue aiming at ensuring the secure configuration of the system, additional security services are necessary. Note that the provision of many of these traditional security services is based on cryptographic keys and identifiers. We will provide an overview of them shortly.
a) Privacy and confidentiality refers to the protection of data, identity, and context information to prevent attackers from eavesdropping on communication. For instance, data confidentiality is achieved by means of encryption algorithms such as the Advance Encryption Standard (AES).
b) Data integrity refers to the protection of data from unauthorized manipulation by means of, e.g., a message authentication code.
c) Identification and authentication addresses the techniques used to ensure validation of different medical events, user identities, and exchanged data. Identifiers should be regulated and standardized in order to ensure interoperability and unambiguous identification as required by HIPAA. Identities should be linked to some cryptographic keying material in order to ensure authentication.
d) Auditing refers to the techniques used to log all data accesses and it is required to fulfill the HIPAA requirements on accountability and provide a traceable record in case of misuse.
e) Access control techniques are necessary to authorize access to patient's EHI and BSN. In addition, access control policies are to be defined addressing issues such as access control priorities and delegation as defined in R. J. Anderson, "*A security policy model for clinical information systems*," sp, p. 0030, 1996 IEEE Symposium on Security and Privacy, 1996; and K. Sohr, M. Drouineaud, G. Ahn. "*Formal specification of role-based security policies for clinical information systems*" ACM Symposium on Applied Computing, 2005, Santa Fe, N. Mex., Mar. 13-17, 2005.

Security and privacy is essential in the medical domain in order to fulfil legal requirements such as HIPAA in USA or the European Directive 95/46 on data protection in Europe. In this context, end-to-end security between medical sensor nodes (or devices) and back-end healthcare services in hospitals is a problem of paramount importance that is currently unsolved. End-to-end security must be independent from the set of sensor nodes used to monitor a patient, and independent from the healthcare service used during the care cycle. This requirement includes (i) the secure association of body sensor network s, (ii) the secure storage of medical related information in the body sensor network, (iii) the unambiguous, but at the same time privacy-aware identification of patients in the whole system, and (iv) the secure transmission of patient information between sensor nodes and healthcare services.

Related known prior art technologies do not solve these problems:

US Patent Application 2007/0043594 describes an electronic healthcare delivery system comprising: (i) a NFC (near field communications) controller chip; (ii) a smart card controller chip; (iii) a wireless peer-to-peer communication protocol; etc. Although the goal of this system is to enable pervasive healthcare, there are some basic differences and shortcomings within this prior art. First, it must be pointed out that this system relies upon NFC technology. Importantly, this patent application does not address security issues, e.g., key distribution, body sensor network association, end-to-end security in pervasive healthcare at all. Likewise, this patent application does not disclose wireless sensor networks and body sensor networks at all.

DE 20008602 U discloses a system in which patient's vital signs, measured by a set of ECG sensors carried by a patient, are linked to the patient's identity. The patent application discloses a card reader to enable patient identification. However, this system fails to disclose end-to-end security and secure body sensor network association.

US 2005/10245995 A1 discloses a data transmission unit for wireless communication with an electromedical implant and a data acquisition and evaluation center. This system fails to disclose an end-to-end security protocol from medical sensor networks including key distribution in body sensor networks, body sensor network association, body sensor network identification and end-to-end security.

US 2003/10229518 A1 discloses a method for recording of patient actions. The system provides a medical equipment to identify a patient so that the data obtained during the use of the medical equipment is attributed to the patient. This system fails to disclose a system for identifying body sensor networks and enabling end-to-end security from body sensor networks to back-end medical systems.

U.S. Pat. No. 6,564,056 B1 describes a controller that administers the devices that are registered to the controller. Each device is registered to the controller by inserting a memory into the controller's card reader. Communications between the controller and devices are secured by using the devices' identifiers as encryption keys. This application fails to disclose a card reader that identifies and registers body sensor network devices, but identifies the body sensor network user.

US 2002/0188473 describes a system that includes patient identification and allows the user to have access to the patient's medical history. The system is based on a smart card. This system fails to address wireless sensor networks and body sensor networks, body sensor network identification, sensor node identification, secure body sensor network association, and end-to-end security between sensor nodes and medical back-end systems.

WO2007/149850 A2 describes a key distribution method that allows any pair of devices in a hospital to agree on a common key in a distributed manner. In this manner, this patent application guarantees basic security services between sensor nodes or between a sensor node and a bedside monitor. However, the important security gap of end-to-end security is still unresolved.

WO2008/014432 A2 describes a method to enable patient identification based on body coupled communications (BCC). In this patent application, every patient carries a body-coupled communications tag. When a patient wants to make use of a specific medical device or the like, the medical device communicates with the body-coupled communications tag by means of body coupled communications to receive the patient ID. In this manner the medical device can make use of the patient's identification information to personalize its measurements or to attach the patient's identification to the measured vital signs before forwarding them to a doctor. Although this approach allows for the identification of patients in a very simple manner, security threats to the system are not taken into account. For instance, an intruder, Bob, might steal Alice's tag and read out Alice's identification information. Afterwards, Bob might impersonate Alice or even get access to Alice's personal medical information. This application addresses the problem of end-to-end security between body sensor network nodes and back-end healthcare services. To this end, this application solves the following security issues:

1. Secure setup of a body sensor network—in the sense that all the communications between all the devices in a body sensor network are secure with respect to authentication and confidentiality;

2. Unambiguous identification of patient—in the sense that a patient is unambiguously identified in the whole system including body sensor networks, back-end security services, etc; and 3. Secure storage of medical related information, so that only authorized personal can have access to it.

SUMMARY OF THE INVENTION

The secure end-to-end patient healthcare system is based on the use of a personal security manager PSM in a body sensor network BSN that carries a patient's information, e.g., identifier and/or medical related information, in a secure manner. The personal security manager can communicate in a secure manner with the rest of sensor nodes WMS within the body sensor network, e.g., medical sensor nodes or monitoring devices, and transmit real patient identifiers, which are recognized in the whole system including back-end systems, by means of body-coupled communications BCC. BCC is the preferred technology, but others, such as Near Field Communications NFC or the like, could be used as well. Additionally, the personal security manager also carries security information including patient identifier, public key, etc. . . . , that allows the personal security manager to authenticate the identity of the patient and enable end-to-end security with the back-end system. Security between the PSM and back-end systems might be based on a public-key infrastructure or based on a trust-third party (such as Kerberos computer network authentication protocol) or further combinations.

Besides the aforementioned technologies that are used for transmitting the users' EHI, the end-to-end security system makes use of two additional technologies, namely body-coupled communication BCC and smart cards, for the secure and transparent identification and formation of a BSN, as well as for the secure storage of security material and EHI. BCC is a low-energy on-body communication that uses the human body as physical networking layer for transmitting data between devices directly attached to a patient's body. This technology saves both energy and spectrum and improves the security level when compared with traditional wireless communication due to the low energy requirements and on-body communication nature that makes it more difficult to eavesdrop on communications. Hence, it can be used by WMSs belonging to the same patient to exchange sensitive data, enable BSN association, i.e., assigning a WMS to a BSN, or exchanging medical data. Smart card technology provides a secure medium to store critical information in a secure manner as well as user authentication. A smart card provides the cryptographic capabilities to allow for authentication and safe data storage.

The combination of BCC and smart card technology provides a strong authentication and identification mechanism. The strong security features of a smart card such as PIN-based access control or embedded cryptographic algorithms allow for secure storage of private information, e.g., passwords. The inherent privacy-aware communication properties of BCC provide a secure transmission medium that makes eavesdropping difficult. For instance, we can imagine a user carrying an identification token with both BCC and smart card capabilities. The user might store on the smart card information such as passwords or private data. This information can only be retrieved from the smart card, e.g., via a BCC link after successful identification and authentication.

A health care card HCC, e.g., a smart card, may be plugged into a personal security manager PSM to provide a link between the body sensor network and back-end security domains that solves the above security issues. The personal security manager carries the patient's information, e.g., name, medical related information, passwords, etc. on a healthcare card in a secure manner which i) includes functionalities to enable the secure association of body sensor network nodes and transmits regulated patient identifiers that are recognized in the whole healthcare system by means of body coupled communication BCC in a secure way as described above. Only wireless medical devices associated to the same BSN and holding the necessary credentials can retrieve private information from the HCC plugged into the PSM via the BCC link, and ii) carries patient information, e.g., patient identifier, patient's public key, etc., that allows the personal security manager to authenticate the identity of the patient and enable end-to-end security between body sensor network nodes and healthcare services. The personal security manager can be implemented on a node with wireless and body-coupled communication interfaces and may include a security module to enable security functionalities in inter- and intra-body sensor network communications.

Some of the security functionalities are physically separated from other components within the system and may be stored on the health care card, increasing both the flexibility and worth of the system.

The principles disclosed in this invention can be applied to medical body sensor networks and devices to enable end-to-end security in ubiquitous patient monitoring systems, such as the care cycle.

A body sensor network BSN is a particular wireless ad hoc network composed of wireless sensors WMS adapted to be attached to a patient's body and may also include a number of wireless medical devices in close vicinity, as shown in FIG. 1. Wireless sensor nodes, e.g., wireless medical sensors WMS, measure a patient's vital signs and transmit them to a PDA or bedside monitor that displays them and forwards them to a central storage unit or the like.

This comprehensive security system overcomes the previous challenges and enables effective and secure access to personal medical data in pervasive medical sensor networks. The system combines existing technologies, such as body-coupled communication and the concept of the digital healthcare card, with distributed security solutions to enable secure body sensor network association, efficient distributed key agreement and access control in body sensor networks, unambiguous patient identification, and end-to-end security across the pervasive healthcare scenarios. This system provides user-friendliness, performance and security, which are especially suitable for resource-constrained wireless medical sensors.

It is an object of the present invention to provide an apparatus and method that provide secure end-to-end communications between all parts of a communications network for healthcare, from the individual wireless medical sensors of a body sensor network to the back-end services.

According to a first aspect of the present invention, a secure end-to-end patient healthcare system, includes
  one or more wireless medical sensors adapted to be attached to a patient's body and in communication with each other forming a body sensor network within a wireless medical sensor network including one or more body sensor networks;
  $\lambda$-secure keying means incorporated into each of said wireless medical sensors for enabling secure communications between said wireless medical sensors, and
  a personal security manager within the body sensor network and in communication with said one or more wireless medical sensors within said body sensor network, said personal security manager providing secure communications with backend services and providing security relationships within said body sensor network by means of said $\lambda$-secure keying means,
  wherein said $\lambda$-secure keying means are such that a coalition of no more than $\lambda$ compromised wireless medical sensors conceals, e.g., reveals nothing, about a pairwise key between any two non-compromised wireless medical sensors and provides perfect resiliency to node compromise until $\lambda+1$ wireless medical sensors have been compromised.

The wireless medical sensors and personal security manager may be adapted to communicate by means of body coupled communications.

The system may further include a healthcare card plugged into the personal security manager, wherein the healthcare card includes information for unambiguous user identification and security information for secure communication with the backend healthcare services, wherein the personal security manager includes a certificate issued by a local trust center, and wherein the system is adapted to execute a security protocol for auditing, access control and privacy protection, and mutual authentication of the personal security manager with the healthcare card.

The information from the body sensor network may be linked to the patient's identity, wherein said patient healthcare card HCC and said personal security manager PSM form an extended personal security manager PSMx, see FIG. 2, for connecting a number of wireless medical sensor network security domains to a pervasive healthcare system. The extended personal security manager may be adapted for:
  storing the certificate issued by the local trust center,
  storing the $\lambda$-secure keying means for establishing an end-to-end security communication issued by centralized healthcare services, and
  implementing the security protocol to enable mutual authentication of the extended personal security manager and the healthcare card, end-to-end security, auditing, and management of context access control and privacy policies.

The extended personal security manager may be adapted for authenticating the personal security manager of the patient and patient's healthcare card when the patient joins the medical sensor network.

The personal security manager may include a smart card reader adapted to receive the healthcare card, and wherein the healthcare card may include individual identification information and/or medical information and/or security material and/or security policies.

The personal security manager may include a user's name, identifier, security material, medical record or access control policies for different medical sensor networks.

The extended personal security manager may include identification for a global user, patient area network, and individual electronic healthcare information EHI. The electronic healthcare information EHI may come from the patient area network.

The security information stored on the healthcare care may be provided for identifying and authenticating the user and for acting as a bridge between the patient's body sensor network and centralized or backend healthcare services. The body sensor network may be the same as the patient area network.

The extended personal security manager may be a mobile phone with an additional smart card slot for the healthcare card.

The secure end-to-end patient healthcare system may further include an autonomous secure domain formed by the wireless medical sensor associated with a patient area network, wherein the extended personal security manager is the patient area network's trust center and is adapted for controlling the secure association or revocation of the patient area network's members.

The extended personal security manager and wireless medical sensors may be adapted for securely storing exchanged information and actions carried out in the body sensor network on the patient's healthcare card even if connectivity to the medical sensor network trust center is lost.

According to a second aspect of the present invention, a method for secure end-to-end patient healthcare communication in an end-to-end patient healthcare system includes the steps of: storing a certificate issued by a local medical sensor network trust center on the personal security manager; storing security means on the personal security manager to establish an end-to-end security communication issued by centralized healthcare services; and implementing a security protocol to enable mutual authentication of the personal security manager and a healthcare card, end-to-end security, auditing, and/or management of context access control and privacy policies.

According to a third aspect of the present invention, a personal security manager for a secure end-to-end patient healthcare system, wherein the personal security manager is within a body sensor network and in communication with one or more wireless medical sensors within the body sensor network, wherein the personal security manager provides secure communications with backend services and provides security relationships within the body sensor network by means of λ-secure keying means, wherein the one or more wireless medical sensors are adapted to be attached to a patient's body and in communication with each other to form the body sensor network within a wireless medical sensor network including one or more body sensor networks; λ-secure keying means incorporated into each of the wireless medical sensors for enabling secure communications between the wireless medical sensors, and wherein the λ-secure keying means are such that a coalition of no more than λ compromised wireless medical sensors conceals, e.g., reveals nothing, about a pairwise key between any two non-compromised wireless medical sensors and provides perfect resiliency to node compromise until λ+1 wireless medical sensors have been compromised.

A λ-secure key establishment refers to a key establishment handshake exhibiting the λ-secure property. A typical example consists of a symmetric bivariate polynomial f(x,y) of degree λ over a finite field Fq where q is large enough to accommodate a cryptographic key. This polynomial is the root keying material in the λ-secure system. From this root keying material, the system's central authority can derive λ-secure keying material shares. Each entity (e.g., sensor node) in the system will carry a λ-secure keying material share. For instance, from the above root keying material f(x,y) an entity with identifier ID would carry the λ-secure keying material share f(ID,y), i.e., the original bivariate polynomial evaluated in x=ID.

Any pair of entities in the system, e.g., ID_A and ID_B carrying f(ID_A, y) and f(ID_B,y) respectively can agree on a common pairwise key as follows:

they exchange their identifiers they exploit their alpha-secure keying materials together with the identifiers. In this specific case, entity A takes its alpha-secure keying material (f(ID_A,y)) and evaluates it at y=ID_B, i.e., the identifier of the other party. The result is f(ID_A,ID_B).

Entity B does exactly the same with its alpha-secure keying material share and the identifier of the other party. The result is f(ID_B, ID_A).

Since the root keying material is a symmetric polynomial, the result obtained by both entities is identical, i.e., f(ID_A,ID_B)=f(ID_B,ID_A)=K. K is the common key shared by both parties. This key is used to provide further security services.

The system might make use of other λ-secure key establishment protocols, i.e., other cryptographic protocols with the λ-secure property. It may be also based on polynomials, but with other features to improve, e.g., its resiliency depending on deployment models, providing more advanced security services such as access control or more efficient performance. For instance, deployment models with a (multiple) hierarchical structure have been proposed to be used in the medical domain. These schemes provide a higher security level since, e.g., they introduce a higher amount of keying material in the system or a pairwise key between two entities is computed as a combination of the keys generated from several independent λ-secure security domains. λ-secure schemes used in the end-to-end security system can be adapted as well to provide further security services such as access control or (privacy-aware) identification. This is achieved by linking the λ-secure keying material with identification information or access control roles. λ-secure schemes might be also adapted to minimize computational requirements, e.g., by using combinatorial techniques based on finite projective planes, key segmentation techniques, or identifier segmentation techniques.

The use of λ-secure techniques allows two entities to agree on a pairwise key, i.e., a key shared between two entities. For instance, let's imagine two persons, Alice and Bob, sharing the symmetric key, K. If Alice wants to send a message to Bob in a confidential manner, Alice uses a symmetric encryption algorithm to encrypt the message with the key K. Bob is able to decrypt it with the same key. In this case, this key is pairwise since it is shared only by Alice and Bob.

It shall be understood that the claimed method has similar and/or identical preferred embodiments as the apparatus and as defined in the dependent claims.

BRIEF DESCRIPTION OF THE DRAWINGS

These and other aspects of the invention will be apparent from and elucidated with reference to the embodiment(s) described hereinafter. In the following drawings:

FIG. 13 provides a table illustrating the performance comparison of some security primitives on MICAz and uPD789828 in accordance with an embodiment of the invention; and FIG. 14 provides a table illustrating memory resource assignments in sub-secure domains of a multidimensional λ-secure key establishment in accordance with an embodiment of the invention.

DETAILED DESCRIPTION OF THE INVENTION

The secure end-to-end patient healthcare system is based on the use of a personal security manager PSM or body sensor network BSN controller that carries a patient's information, e.g., identifier, medical related information, in a secure manner. The personal security manager can communicate in a secure manner with the rest of sensor nodes within the body sensor network, e.g., medical sensor nodes or monitoring devices, and transmit real patient identifiers, which are recognized in the whole system, including back-end systems, by means of body-coupled communications BCC. Additionally, the personal security manager also carries information, to include patient identification information, public key, etc. . . . , that allows the personal security manager to authenticate the identity of the patient and enable end-to-end security with the back-end system.

Figure 1:
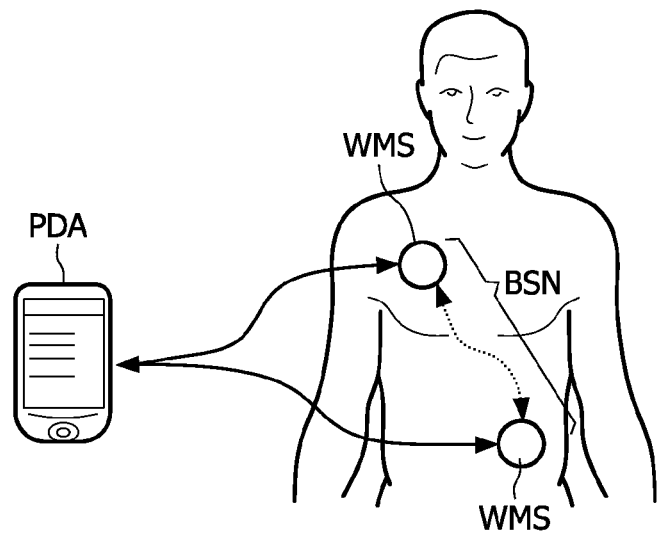
FIG. 1 illustrates a body sensor network for a secure end-to-end patient healthcare system in accordance with an embodiment of the present invention.
Figure 2:
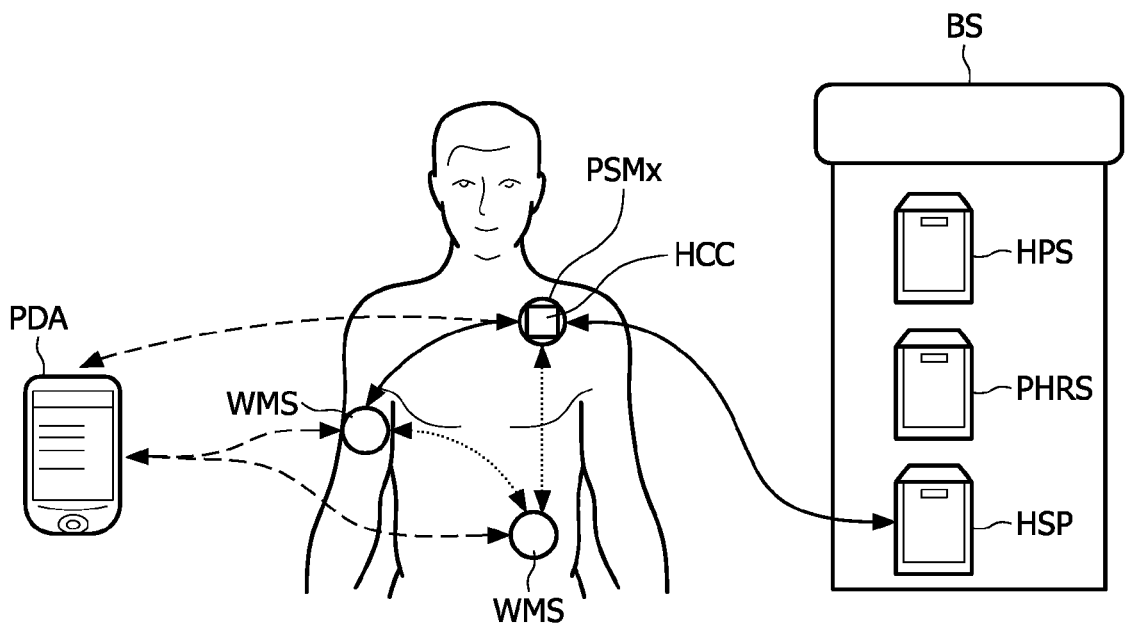
FIG. 2 illustrates the components for a secure end-to-end patient healthcare system in accordance with an embodiment of the present invention.

The security architecture comprises several physical elements, as shown in FIGS. 1 and 2: Sensor nodes, e.g., WMSs, are used to monitor patient vital signs, and may be distinguished into two or more different types. On the one hand, some medical sensor nodes are used to sense and transmit a patient's vital signs. On the other hand, monitoring devices, such as PDAs or monitors, communicate with the medical sensor nodes and display the patient's vital signs. Communications may be carried out by means of a wireless interface. Additionally, some sensor nodes may have body-coupled communications or inductive capabilities.

Healthcare services are back-end services BS, e.g., a healthcare provider service HPS, a personal healthcare record service PHRS and/or a healthcare security provider HSP. These services manage, store and provide access to the patient's medical data, so that medical data is available 24/7.

Personal security manager organizes the security relationships between medical sensor nodes, monitoring devices and healthcare services. Therefore, the personal security manager plays a role of special importance. Note that the security infrastructure might not include all of these physical elements, i.e., some of the security services or monitoring devices might be missing.

In FIG. 2 communication with healthcare services is indicated by a drawn through line, BCC communication or inductive communication is indicated by a dashed line, and wireless communication is indicated by a dotted line.

Cryptographic Elements Involved in the Security Architecture

The security architecture requires different elements that are described below. Most of these elements and functionalities are implemented in the personal security manager as it is used as a link between the sensor nodes and healthcare services (see FIG. 3) from the security point of view.

1. An activation PIN is used to authenticate the user before use. This functionality is specific for the personal security manager PSM and is used to prevent unauthorized persons from having access to the personal security manager.

2. Keying Material KM enables secure communications between sensor nodes, or between sensor nodes and the personal security manager.

3. Patient's Identification Information (digital identity) is used to identify a patient and comprises:

a. A patient's identifier;

b. Cryptographic information linked to the patient's identifier. A possible embodiment is the use of a pair public/private keys bound to the patient's identity. The authenticity and validity of these keys rely on a public key infrastructure. Another embodiment would be the use of a third trust party. In this case, a unique symmetric secret linked to the patient would be used to establish further security relationships based on the online trust center.

c. Digital identity controller (digital identity manager) may be used to handle the disclosure of the patient's digital identity. The validity of the patient's identifier and related cryptographic information, e.g., public key, relies on a healthcare security server that manages the security relationships in the whole system. Therefore, these functionalities may be implemented both in the personal security manager and the healthcare security server. The digital identity controller resides in the personal security manager.

Depending on the particular embodiment, some of the above elements might not be present. Different embodiments of the invention may require further identification elements, e.g., biometric identification techniques.

4. The personal security manager may also have a secure memory MEM to allow the secure storage of information such as: medical related information, a patient's digital identity, access control rights, patient's passwords, etc. . . . The secure memory MEM may be embedded in the PSM itself or in the HCC.

Figure 3:
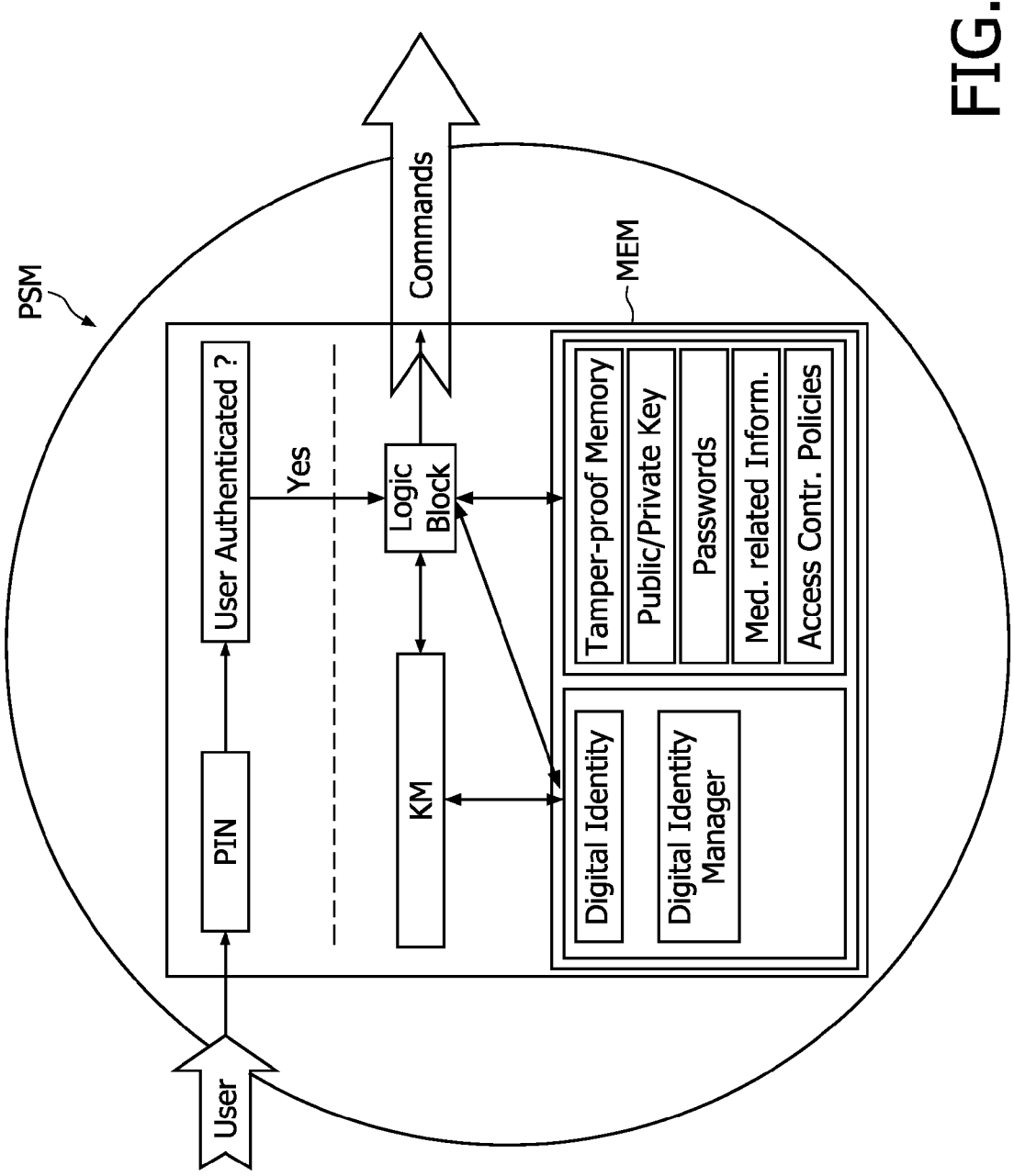
FIG. 3 illustrates the security arrangements within a personal security manager for a secure end-to-end patient healthcare system in accordance with an embodiment of the present invention.

The functionalities of the personal security manager are depicted in detail in FIG. 3. Various embodiments may include a number of unique features, e.g., the personal security manager PSM, which may be activated only after successful input of the user's PIN; the personal security manager may have some intelligence, i.e., a logic block, including the description of security protocols; the personal security manager may include keying material KM to enable secure communication with sensor nodes; the personal security manager may store patient related information including: the patient's digital identity, medical information, access control rights or passwords; and the keying material and logic may be embedded in the personal security manager; however, patient-related information may be stored on a smart card, e.g., a healthcare card HCC. In this manner, the same personal security manager may be used by different patients by replacing the patient's healthcare care in the personal security manager.

Functionalities of the Security Architecture

Figure 4:
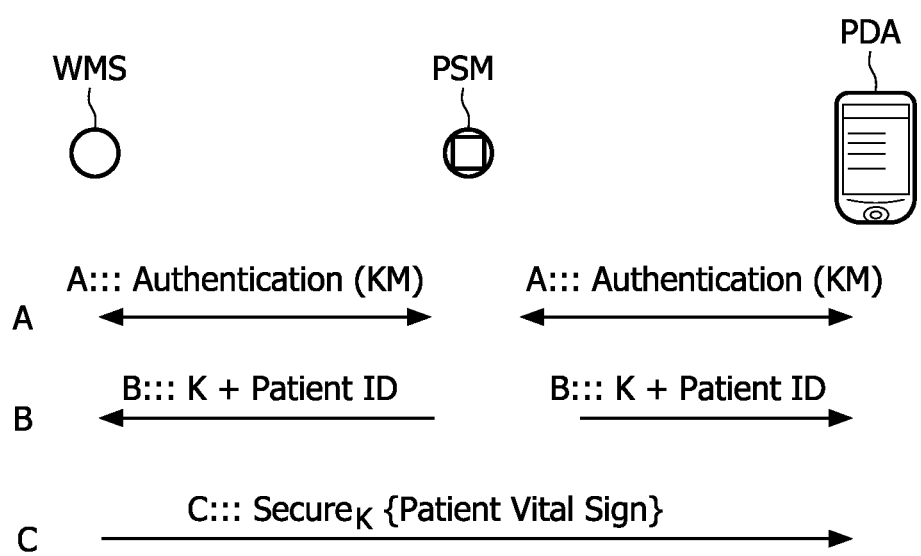
FIGS. 4A-4C illustrate the security protocol arrangements within a body sensor network in accordance with an embodiment of the present invention.
Figure 5:
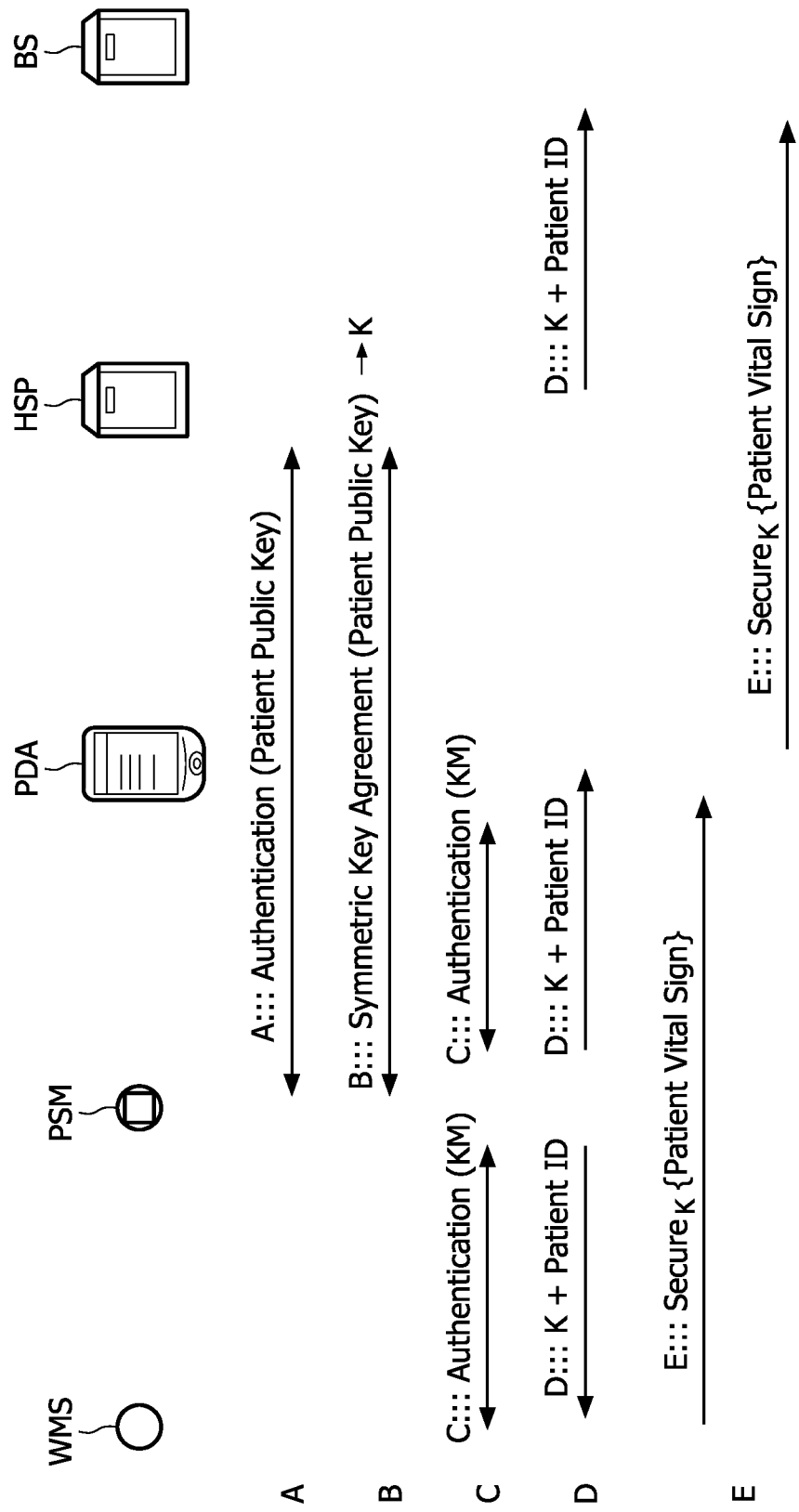
FIGS. 5A-5E illustrate the security protocol arrangements for end-to-end security within a patient healthcare system in accordance with an embodiment of the present invention.

Next, it is described how the personal security manager exploits previous security primitives to manage the security relationships between sensor nodes and healthcare care services. Some of these functionalities and relationships between the different physical elements are illustrated in FIGS. 4 and 5.

1. User authentication—before a personal security manager is activated, a user must authenticate himself by means of a user PIN. The PIN is entered by means of a user interface (UI) or the like. This can be easily implemented if the body sensor network controller PSM is implemented in a mobile phone or the like. The rest of the body sensor network controller functionalities may be operative only after successful user authentication. Depending on the embodiment, the activation of the PSM might only be possible if the HCC is plugged in, since the HCC implements the user authentication functionalities.

2. Secure automatic setup of a body sensor network—after activation, the personal security manager may be used to setup a body sensor network in a secure manner. To this end, when a patient arrives at a hospital or the like, the patient may receive a personal security manager with the functionalities described above. Identifiers of the doctors, nurses etc. that have access rights to the patient body sensor network may also be loaded during admission. Additionally, patient related information, e.g., identifiers, medical related information, may be loaded manually or from the hospital server. In this case, the personal security manager may implement all the functionalities depicted in FIG. 3 in a single device.

In addition, the personal security manager may include a card reader for healthcare cards, such as a smart card. In this case, all of a patient's medical related information, e.g., patient's digital identity, medical related information, public and private key, passwords, etc, may be stored in the smart card HCC. This information may be accessed only after inserting the patient's healthcare card in the personal security manager. Some of this information may be always available, while the access to other information might require different levels of authorization, e.g., different PINs. Once the patient carries her personal security manager, she can be attended. To this end, doctors may attach several sensor nodes, e.g., ECG, $SpO_2$, to her body as well as a monitoring device. To associate sensor nodes and monitoring devices to the patient's body sensor network, the doctor may make use of the personal security manager as described in FIGS. 4 and 5. This association between the personal security manager and the body sensor network may make use of body-coupled communications BCC, inductive communications, e.g., near field communications, or the like. The use of BCC has inherent advantages as only devices attached to the same body can communicate with each other. In addition to the association features described in FIGS. 4 and 5, the mechanism described is secure due to the following specific aspects:

FIG. 4A—The personal security manager PSM and sensor nodes WMS use the keying material KM to agree on a common secret and authenticate each other. In this manner, the personal security manager guarantees that only authenticated medical devices PDA are allowed to join to the patient's body sensor network. Access control policies stored on the PSM (or HCC plugged into the PSM) might also be used to decide whether a sensor node is authorized to join the BSN or not.

FIG. 4B—The personal security manager can access the patient's related information, including identifier, or personal health record. Therefore, the personal security manager makes use of real patient information to identify the body sensor network in an unambiguous form and simplifies the care-cycle. In particular, the personal security manager can (1) derive a temporal patient identifier (patient ID) for the patient used to identify the body sensor network. Temporal patient identifiers are changed periodically to prevent user's privacy sphere and prevent tracking, (2) set a BSN network key K that is used for communications within the BSN security domain. All the communication between BSN members might be secured based on this key allowing for broadcast.

(3) transmit the patient's information (in response to a request) to the medical sensor nodes in a secure manner based on the keying material. Transmitted information may include the temporal patient's identifier or the identifiers of the doctors, nurses or other personnel PDA that have access to the medical information (see FIG. 4B).

FIG. 4C—Finally, the medical sensor nodes may transmit the patient's vital signs to the monitoring device in a secure manner by using the key K, which was distributed by the personal security manager previously, to enable basic security services.

3. Unambiguous patient identification and access to backend healthcare services represents a problem for prior art systems, as it is difficult to bind a temporal patient identifier with the vital signs measured by a random set of sensor nodes to such back-end systems, e.g., the personal health record stored in a server.

This invention overcomes this problem as the personal security manager acts as the security link between the sensor nodes and back-end systems. On the one hand, a personal security manager has keying material that enables secure communications with the sensor nodes. On the other hand, the personal security manager may also have the information required to identify a patient. This information may be loaded during patient admission or after plugging the patient's health card into the personal security manager reader.

FIGS. 5A-5E depict the protocol carried out by sensor nodes, personal security manager, and back-end systems to achieve end-to-end security and unambiguous patient identification independently from the set of sensor nodes that may be used to monitor a patient. FIG. 5A illustrates the connection of the personal security manager to a healthcare security provider HSP to authenticate the identity of the patient based on the public key stored in the memory of the personal security manager. FIG. 5B represents the negotiation of different security parameters, e.g., a symmetric key K that may be used to enable end-to-end security. Afterwards, FIGS. 5C and 5D illustrate the secure association of sensor nodes to the patient's body sensor network, as described above, and between the HSP and the BS. Finally, FIG. 5E illustrates how the patient's vital signs are not only sent to monitoring devices PDA, but also to healthcare services in a secure manner.

4. In addition to previously detailed operation issues, the security architecture may enable further security services, e.g.:

Secure Memory—which may be used to store confidential information such as passwords or medical related information. The access to this information may be restricted to authorized users. Different levels of authorization are possible by means of different PINs. A user carrying a personal security manager can make use of it to store passwords in a secure manner.

Secure login—may be used by a user carrying a PSM with BCC capabilities. For instance, imagine that the user wants check his healthcare record on the web. The login information (e.g., username+password) is stored on the PSM. The personal computer used to look up the healthcare record may incorporate a BCC interface. When the PC switches on the BCC, the PSM can authenticate the PC based on the distributed keying material. Afterwards the user can check his healthcare record without manually entering his username and password. This information, which is stored on the PSM, is transmitted directly to the PC via BCC. The same approach might be used to access the personal e-mail, enter home, etc.

Digital Identity—A user may make use of a personal security manager for identification purposes, and thus, the security module implements a sub-module. In general, the digital identity of a patient or person may be linked to a public/private key.

Network control—The personal security manager may be used to store useful information such as:
  i. sensor nodes that comprises the body sensor network;
  ii. monitoring devices that monitor the patient's vital signs;
  iii. other events that occur during the monitoring of the patient such as unusual behavior of sensor nodes. This information may be used to detect defective or compromised sensor nodes. In such an event, the compromised device should be removed from the BSN and BSN's/user's information such as identifier or BSN network key K should be updated in order to protect the user's privacy.

Key Distribution in Pervasive MSNs

Key distribution is fundamental to enable end-to-end security. However, the choice of the best key distribution approach depends on the technical restrictions and operational requirements of both an MSN and the healthcare system.

Reliable and secure communication between any pair of WMSs in an MSN requires the ability of WMSs to directly establish a pairwise key without relying on an online trust center or public key infrastructure as described above. The present system may use two different types of key distribution approaches to handle cryptographic keys depending on the operational requirements of the healthcare application desired. On the one hand, we have so-called personal BSNs that always comprise the same set of WMSs, as they are always used by the same user, e.g., at home. Key distribution for these personal BSNs can be solved easily by distributing pairwise keys between all the nodes by means of an out-of-band channel or in a secure environment. Hence, in a BSN with n nodes, each node stores n−1 keys.

On the other hand, in hospitals, retirement homes or fitness centers, MSNs may comprise a large number of WSNs. A subset of WMSs may be randomly picked up from the MSN's pool of WMSs to comprise a BSN. In this situation, key distribution systems based on $\lambda$-secure key distribution systems, such as Blundo polynomials, provide an efficient and feasible solution for efficient key distribution because they require few computational resources and enable full connectivity between any pair of nodes. In this context, every node, z, belonging to the same MSN has a unique identifier $ID_z$ linked to a different but correlated set of keying material, $KM_z$, carried by the node. The different sets of keying material for different nodes are generated offline by a trust center from a keying material root ($KM^{root}$). Whenever a pair of nodes needs to agree on a common key, they exchange their node IDs and use their respective keying materials to agree on a pairwise key for enabling further security services. In one approach, the $KM^{root}$ is a single bivariate polynomial $f(x,y)$ of degree $\lambda$ over a finite field $F_q$, with a sufficiently large q to accommodate a cryptographic key. Each WMS, z, receives from the MSN trust center a set of keying material derived from $KM^{root}$, $KM_z$, e.g., composed of a polynomial share, $f(zy)$, generated by evaluating the original bivariate polynomial in $x=z$. This set of keying material, $KM_z$, is carried during the entire life of WMS z, and the identifier, $ID_z$ can be seen as a serial number that identifies each node in the MSN. This approach where the $KM^{root}$ is a bivariate polynomial can be combined with key segmentation or combinatorial techniques to improve the performance and resiliency of the system in $\lambda$-secure key distribution systems. For simplicity, we consider that each $KM_z$ carried by a WMS is composed of a polynomial share $f(z,y)$.

This approach allows for efficient distributed key agreement, but does not enable lightweight implementation of security services such as access control in MSNs, a key security issue in medical applications. This is due to the unique identifier, z, linked to the $KM_z$ carried by each node z, and that requires a large amount of memory to store access control lists. Furthermore, the use of a single $\lambda$-secure secure domain SD implies that the capture of $\lambda$ WMSs in an MSN SD allows an attacker to compromise the security of the whole MSN.

To overcome both problems, it is possible to take into account the deployment model of target MSNs to distribute additional $\lambda$-secure KM to WMSs in a smart way. To understand this, observe that a WMS belonging to an MSN may be subdivided into several sub-SDs according to different features such as ownership, operational zone or medical specialty. For instance, the WMSs of a hospital MSN can be classified according to (i) location (a medical MSN may comprise several hospitals, and each of these hospitals can be divided into different departments); (ii) medical specialty as departments located in different hospitals may share the same medical specialty; or (iii) operational zone as patients suffering of a specific disease may be treated in different medical departments. The MSN trust center TC (see FIG. 6) can allocate additional $\lambda$-secure keying material to WMSs in order to identify and authenticate to which of the previously-mentioned sub-SDs a WMS belongs in a discrete way. Each feature, j, with $1 \leq j \leq n$, can describe a flat SD or a hierarchical infrastructure of SDs. A flat SD comprises a sub-set of WMSs of the MSN that can communicate with the same probability p, e.g., the WMSs used in the same operational zone. A hierarchical infrastructure of SDs describes relationships between nodes, e.g., due to the WMS location. For instance, the location of a node can be split into hospital and/or department. In this example, it is clear that all WMSs in a hospital must be able to communicate with each other, but also that communications between WMSs belonging to a given department are more frequent as they occur in the same location. In fact, communication between WMSs from different departments may rarely occur, and occur only if, for instance, a patient is moved to another department. The following formula may be used to allocate the sub-identifiers, $ID_{ij}$, for the sub-SDs to a WMS with identifier ID: $ID_{ij}=h(ID|j|i)$.

In this expression, $h(\bullet)$ is a cryptographic hash function, j identifies a WMS characteristic such as location or ownership, and i refers to the level in the hierarchy of SDs, e.g., for the location, hospital is located at level 1, and department at level 2. Note that the keying material linked to each of these sub-SDs may be generated from a different $KM_{ij}^{root}$ such as, e.g., a different bivariate polynomial $f^{ij}(x,y)$, but that the identifiers used in each sub-SD are linked by means of (1) to prevent an attacker from creating arbitrary identities with arbitrary features. Note that the above naming convention might be easily adapted or modified or simplified.

Figure 8:
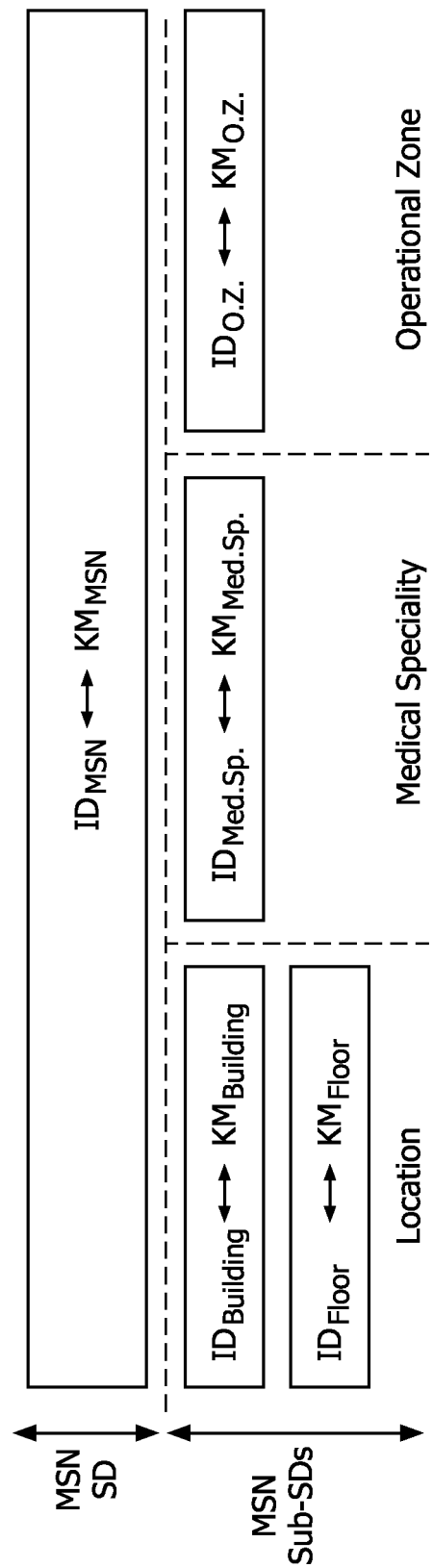
FIG. 8 depicts the information carried by a wireless medical sensor in a particular medical sensor network in accordance with an embodiment of the present invention.

FIG. 8 depicts the information carried by a WMS in a particular MSN. The WMS has a unique MSN identifier $ID_{MSN}$ linked to keying material $KM_{MSN}$. This information enables full interoperability between any pair of WMSs in the same MSN. Note that $ID_{MSN}$ may be allocated to different devices or medical staff in such a way that depends on their digital identity. Additionally, the WMS also carries keying material that identifies and authenticates itself according to three different features, namely location (building and floor), operational zone, and medical specialty.

Figure 9:
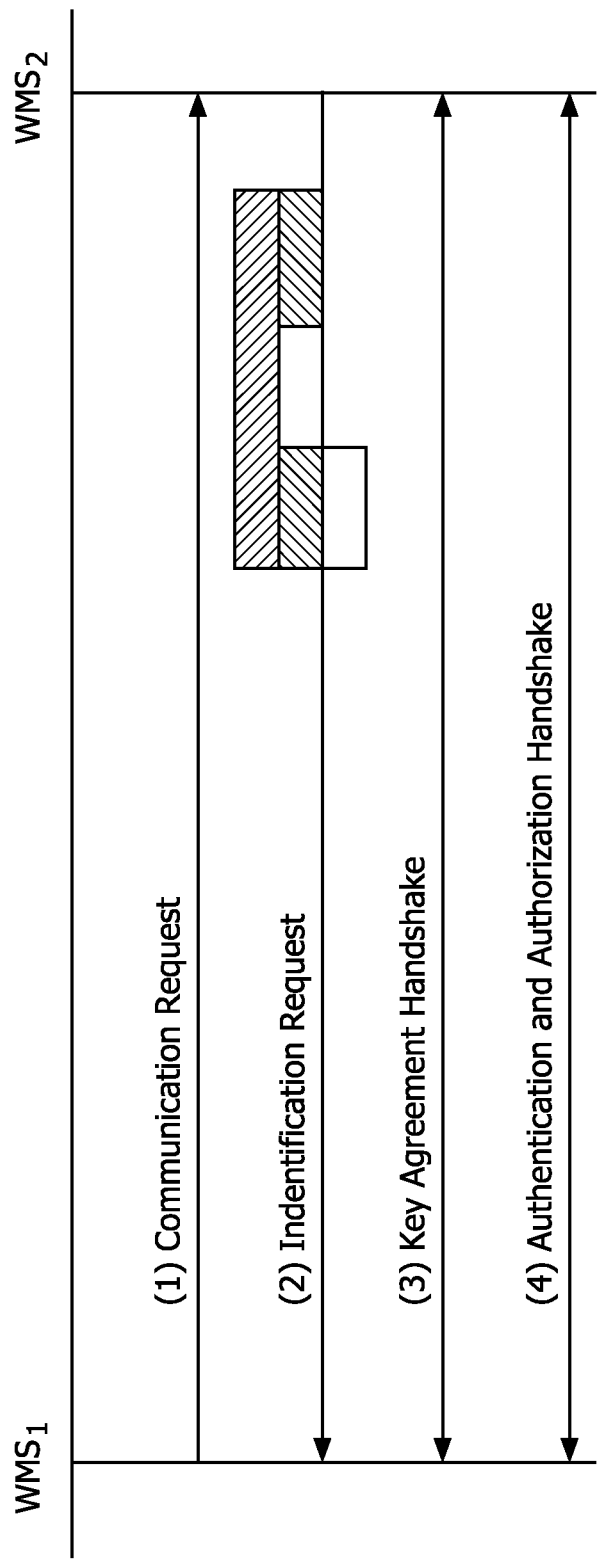
FIG. 9 illustrates the efficient establishment of a secure communication channel between two wireless medical sensors belonging to the same medical sensor network in accordance with an embodiment of the present invention.
Figure 12:
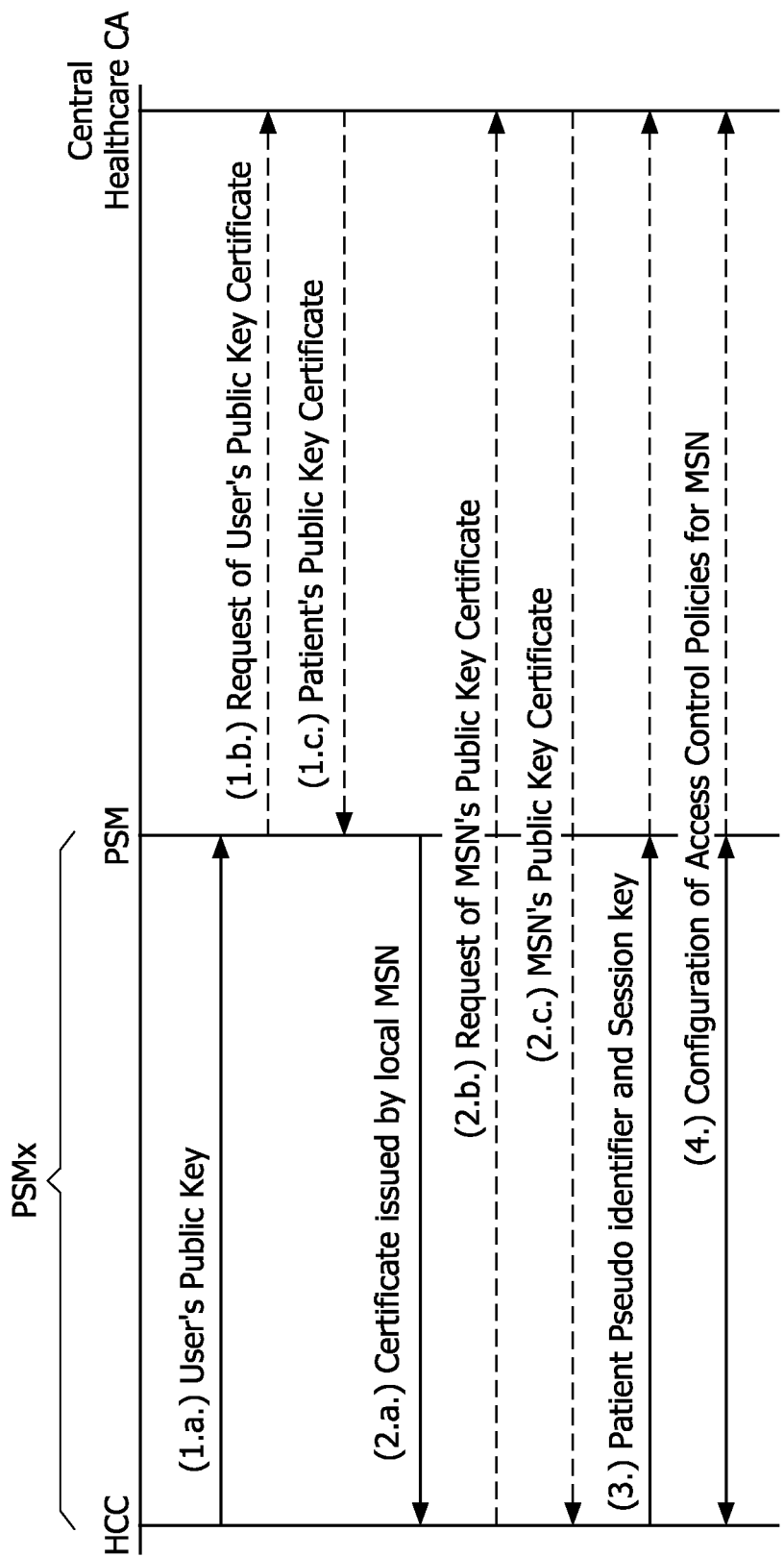
FIG. 12 illustrates the communications between the extended personal security manager and the central healthcare certification authority of the back-end healthcare services in accordance with an embodiment of the invention.

Based on this information, two WMSs belonging to the same MSN can establish a secure communication channel in an efficient way (see FIG. 9). In a first step, $WMS_1$, e.g., a clinician PDA, sends a communication request to $WMS_2$, e.g., an ECG WMS attached to a patient. $WMS_2$ requests the identification of the PDA as belonging to the MSN. Additionally, the access control policies of that patient may require the clinician to have a specific digital identity $ID_{MSN}$ or to belong to the same hospital and operational zone sub-SDs (required roles). In general, any sub-set of sub-SDs might be required to be authorized to carry out a command. This approach allows for cryptographically enforced access control. Thirdly, both WMSs carry out a key agreement handshake. To this end, each WMS computes a partial key, $K_{ij}$, from the keying material linked to each required (sub-)SD, ji, $KM^{ji}$, to be authenticated. $K_{ji}$ is computed by evaluating $KM_{ij}$, i.e., the polynomial share $f_{ij}(h(ID|j|i),y)$, in the identifier of the other party for that (sub-)SD. Both nodes can generate a master key K by hashing all the partial keys in the same order. The master key K will be common to both WMSs, if each of the partial keys is identical. This key is used afterwards to authenticate both WMSs by means of a challenge-response authentication handshake. Successful authentication also implies that the clinician fulfils the access control policies for the patient. Note that the basic key distribution approach of this example can be easily extended to a general multidimensional $\lambda$-secure key establishment $m\lambda KE$ with an arbitrary number of sub-SDs ji where the main ID encodes the digital identity of a device and sub-SDs represent the roles of the device. Furthermore the ID might be used to encode the digital identity of the entity or other information such as access control roles by calculating ID=h (Digital Identity) as described in the state of the art In addition to ensuring secure communication between WMSs, the disclosed security system must enable end-to-end security between WMSs in BSNs and back-end healthcare services. This system uses a public-key infrastructure PKI based solution for this as it allows users to move across MSNs in a secure manner, and thus, ensures interoperability. Observe that other approaches, e.g., based on a trust third party, e.g., Kerberos might be also applied to achieve the same goal. In a public-key based approach, each user in the system requires a pair of public/private keys issued by a healthcare certification authority HSP (centralized or distributed) (see FIG. 6) and linked to the user's identity. This pair of keys is used only during the initial configuration procedure that takes place when a user arrives to a MSN, as described below, so that resource requirements are minimized (see FIG. 6 and FIG. 12). However, ensuring that a user's BSN always contains this pair of keys is a challenging task as the membership of a BSN is unpredictable, as described above. The solution to these issues is presented below.

Secure BSN Association

Figure 7:
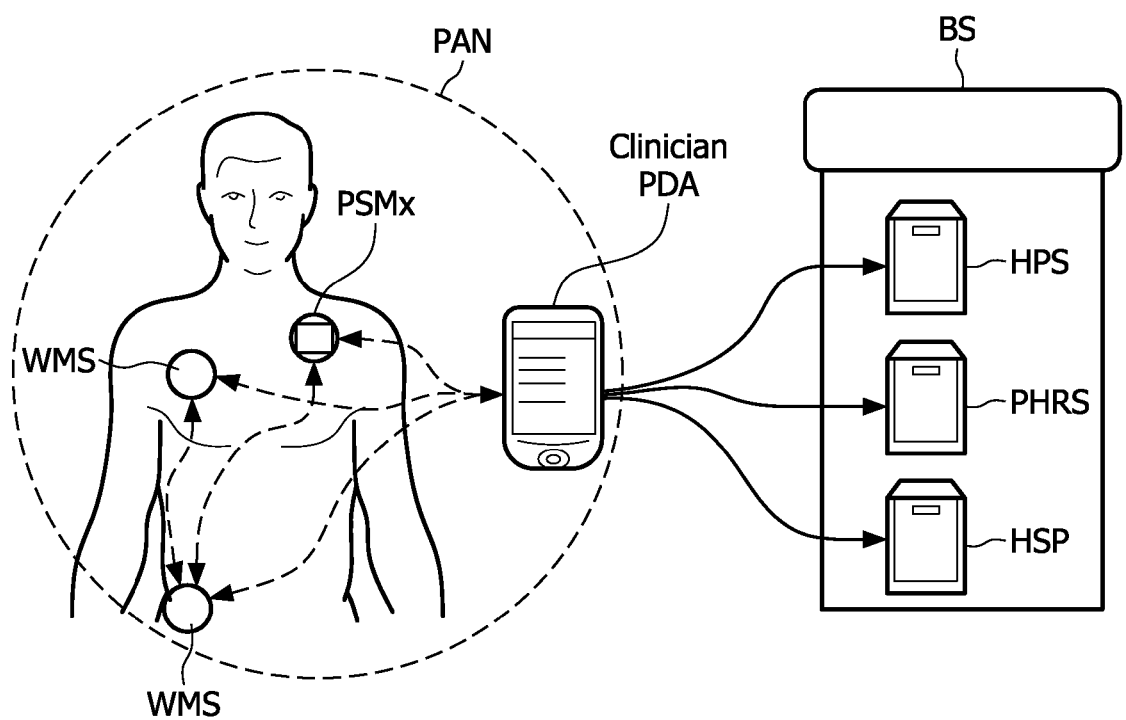
FIG. 7 illustrates the communications links for a secure end-to-end patient healthcare system in accordance with an embodiment of the present invention.
Figure 10:
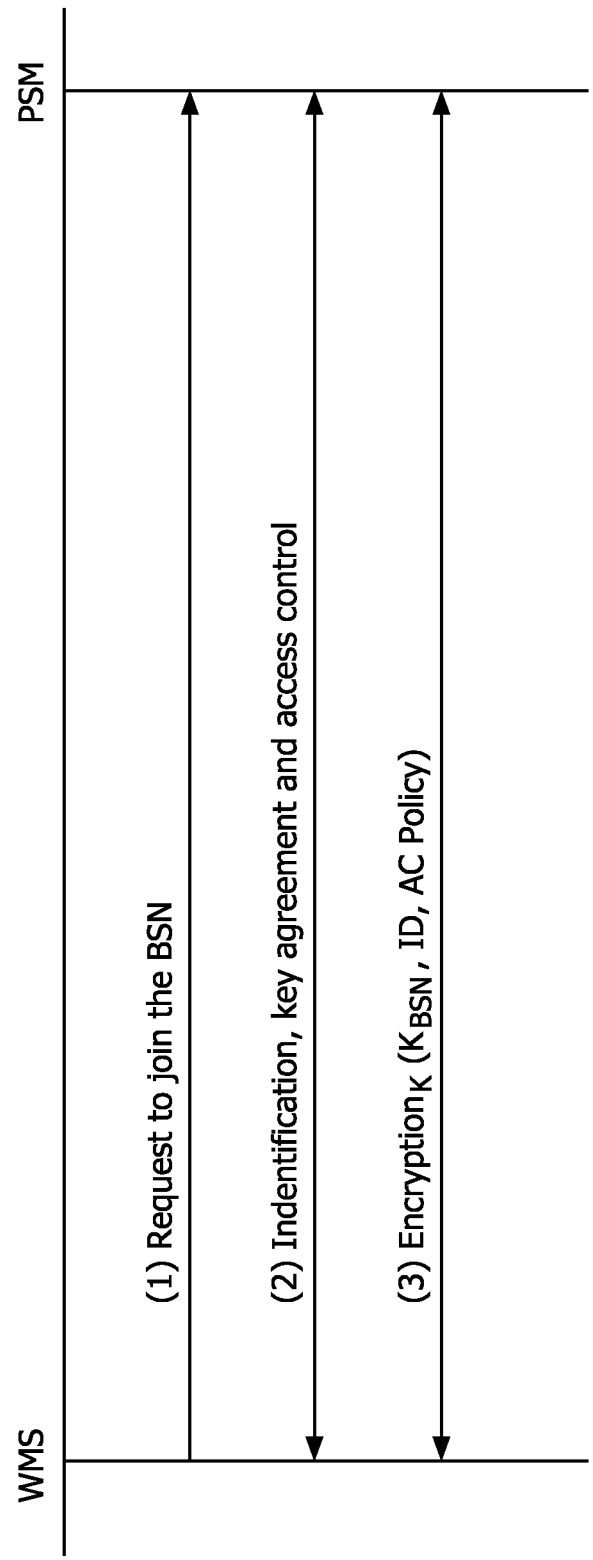
FIG. 10 illustrates the method for enabling secure body sensor network association between a wireless medical sensor and the personal security manager in accordance with an embodiment of the invention.

The disclosed system is based on and extends the BSN association protocol described above for enabling secure BSN association, as depicted in FIG. 10. A special WMS, called personal security manager PSM or extended personal security manager PSMx, (see FIGS. 7, 10 and 11) plays the role of a personal identifier as it is used to transmit the patient's identifier to other WMSs attached to the patient, and thus, linking WMSs to the user's identity. Communication between PSM and WMSs may be based on body-coupled communication, and thus, may be restricted to devices directly attached to a patient's body.

Firstly, before transferring the patient's ID to a WMS or accepting a WMS in the BSN (FIG. 10, step 1), the PSM authenticates and authorizes the WMS according to $\lambda$-secure methods described previously. To this end, the PSM and the WMS may use the $\lambda$-secure keying material that both nodes carry to generate a master key $K_{PSM-WMS}$. Based on this key, both nodes can efficiently authenticate and authorize each other and transmit further information, e.g., user ID, in a secure manner. Additionally, the PSM may play the role of the BSN's trust center that generates and distributes a BSN key, $K_{BSN}$, to all the BSN members. $K_{BSN}$ is the network key of the BSN's security domain and can be used to enable broadcast within the BSN and to convert the BSN in an independent SD, which is controlled by the user's BSN, within the MSN SD.

The network key $K_{BSN}$ in combination with BCC may also enable effortless implementation of a WMS revocation procedure. This is necessary when a node is captured or leaves a patient's BSN. To this end, the PSM sends periodic requests to each member of the BSN over BCC. If the PSM does not receive a reply from any of them, the PSM updates both the user identifier and BSN key, $K'_{BSN}$, in order to protect user's privacy. The new identifier and BSN key are sent to BSN members in a secure manner by using body-coupled communications and the corresponding pairwise key. Finally, the PSM might transmit a random sequence to all WMSs in the BSN. WMSs may synchronously blink following this random sequence in order to allow clinicians to check the correct BSN association of all the WMSs in a simple way.

Unambiguous and Unique User Identification

BSNs must be seen as completely independent SDs in a MSN where the security interactions with other MSN's WMSs and users are handled by means of the PSM. Additionally, the PSM must provide global user and user's electronic healthcare information (EHI) identification, as well as further security services, e.g., auditing, management of access control policies, or end-to-end security.

In order to link the user's vital signs to the user's unique identifier, which is independent of the MSN where the user is located in a specific moment, the disclosed security system may use the healthcare card HCC in combination with the PSM to form an extended personal security manager PSMx. The PSMx connects the different MSN security domains with the pervasive healthcare system, i.e., the PSMx organizes the security relationships between the WMSs that comprise the user's BSN in a specific MSN and back-end healthcare services to achieve unambiguous and unique user identification in pervasive MSNs.

Figure 11:
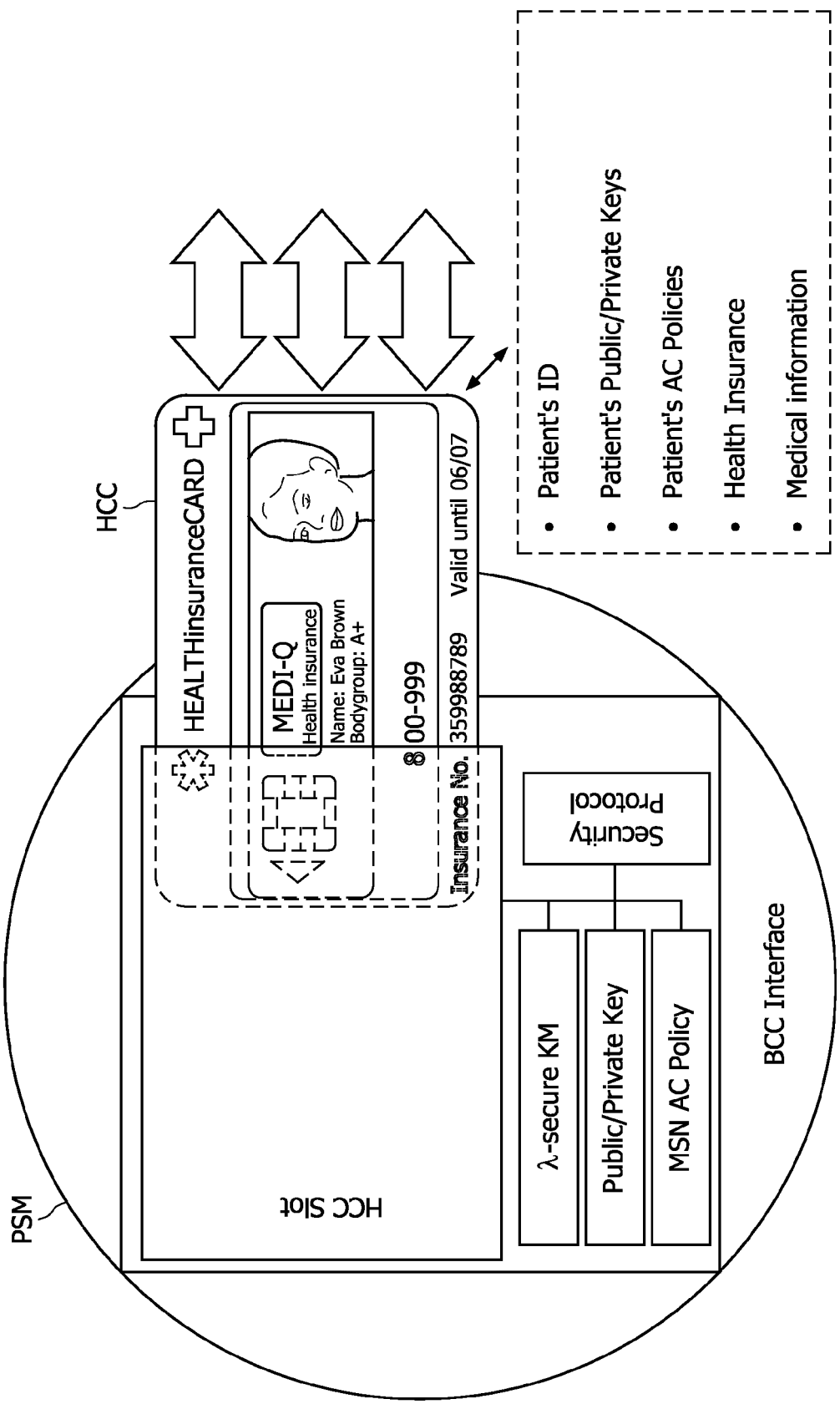
FIG. 11 illustrates the structure of the extended personal security manager in accordance with an embodiment of the invention.

The PSMx may consist of several independent functional blocks (see FIG. 11). Firstly, it may store the $\lambda$-secure keying material KM to enable secure communication with WMSs of the MSN, as described above. The PSMx may be pre-configured with $\lambda$-secure KM or enable its dynamic configuration in a secure environment during the setup phase. The PSMx may also stores a certificate issued by the local MSN trust center. The purpose of this certificate is to allow the user and user's HCC to authenticate the authenticity of the PSM when he joins an MSN. Secondly, the PSMx may implement a smart card reader (HCC Slot) so that the user's health care card can be plugged in. The disclosed system uses the HCC with identification purposes for use in medical applications. Security systems for pervasive healthcare should be fully compatible with it. In one embodiment, the most relevant user medical information will be stored on the HCC, e.g., user's name, identifier, and medical record or access control AC policies for different MSNs. Additionally, the HCC may also store the user's public/private keys issued by the global healthcare CA. Finally, the PSMx may implement a security protocol to enable mutual authentication of PSMx and HCC, end-to-end security, auditing, and management of context access control and privacy policies.

The combination of the HCC with the PSM to create the PSMx ensures interoperability between different MSNs and back-end systems. On the one hand, the security information stored on the HCC identifies and authenticates the user, acting as bridge between the user's BSN and centralized healthcare services wherever the user is located. This includes the use of a regulated user ID, or a temporal pseudonym derived from the identifier according to a regulated procedure, used in the whole system to achieve unambiguous user identification across a variety of application scenarios. The user's public key is used to authenticate the user ID and to setup a secure communication between the BSN and back-end healthcare services. On the other hand, the PSMx, in which the HCC is inserted, stores the λ-secure KM that enables secure communications with WMSs in the same MSN. Hence, this construction allows for the creation of an end-to-end secure link between the WMSs that comprise a user's BSN and the centralized pervasive healthcare services, even if patients move from one MSN to another. Additionally, a PSMx may be switched to accommodate a new patient by exchanging the HCC (see FIGS. 6, 7 and 11). Embodiments of the PSMx might range from a mobile phone with an additional smart card slot for the HCC to a bracelet carried by patients in a hospital.

Additionally, the PSMx can also dynamically manage the access control AC policies (see FIG. 10) for a patient. These access control policies might be combined with λ-secure access control techniques as explained above. In this context, the PSMx can handle the local AC policies in the current MSN with global AC policies controlled by back-end healthcare services. Context-aware techniques can used to improve the access control policies, e.g., to enable access to a patient's BSN to any clinician when an emergency is detected.

Finally, an important feature of our security system is that the BSN forms an autonomous secure domain SD where the PSMx is the user's trust center. Therefore, all actions carried out in the BSN can be recorded on the user's HCC even if connectivity to the MSN trust center is lost. This guarantees auditing of medical actions since the user's HCC can keep a record of all the devices and users who tried to have, or had access to the user's BSN. Furthermore, the technical properties of smart cards prevent unauthorized access to this information.

System Evaluation

The evaluation of the security architecture for MSNs may be carried out from three orthogonal points of view, namely, practical feasibility in professional medical settings, system performance, and security analysis.

Practical Feasibility: Configuration and Deployment

A security system for MSNs must be simple to configure and deploy in order to minimize costs. Additionally, medical staff and users without technical backgrounds must be able to intuitively handle the appliances given to them.

Figure 6:
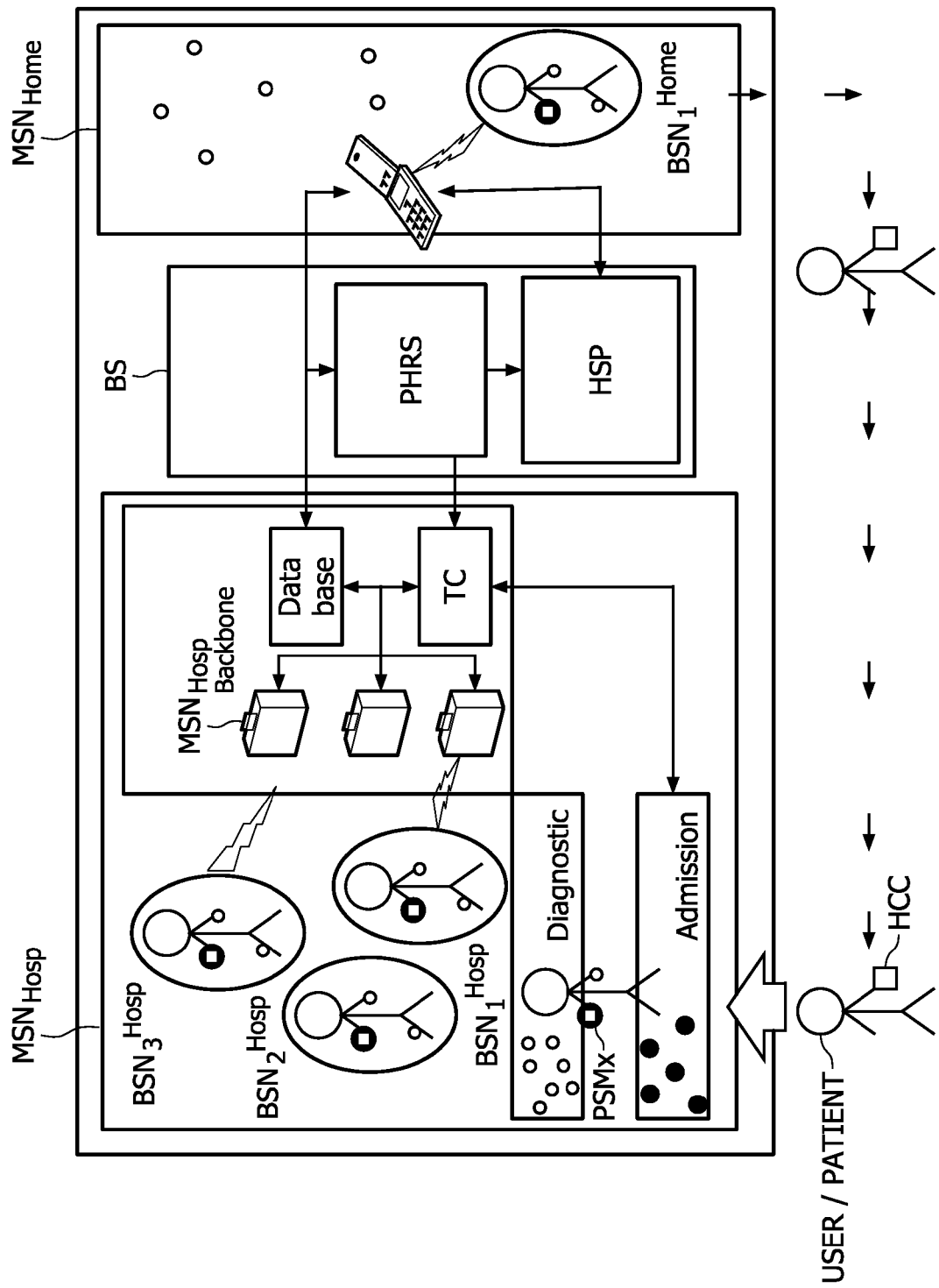
FIG. 6 illustrates a facility incorporating the secure end-to-end patient healthcare system in accordance with an embodiment of the present invention.

In order to show both properties, we will now focus our attention on the system configuration when an elderly user, Robert, goes to the hospital for a professional medical procedure (see FIG. 6). When Robert arrives at the hospital's admission desk, he uses his HCC for identification and payment. Afterwards, the HCC is inserted into a PSM to create a PSMx and a mutual authentication handshake is carried out. The PSMx is configured with the corresponding λ-secure KM to enable secure communications with WMSs, as well as with the local access control policy for that patient. This local policy is stored on the patient's HCC, and in the patient's back-end healthcare record.

After admission, the patient receives a set of WMSs, in Diagnostic, for monitoring his vital signs. Each of the WMSs communicates with the patient's PSMx by carrying out a key agreement, authentication and authentication handshake via body-coupled communications BCC. Each of the WMSs that successfully finishes this step becomes a member of the patient's BSN, and receives the BSN network key and patient's identifier. The identities of each and every WMS are stored on the patient's HCC, including the digital identities of clinician's PDAs used to monitor or treat patients. The hospital's MSN ($MSN_{HOSP}$) may include a number of BSNs ($BSN_{x\,Hosp}$).

The system allows for automatically initiating a BSN in a secure manner, e.g., as a doctor wants to monitor the vital signs of a patient, the doctor briefly touches the patient to establish a BCC channel between the PSMx and PDA. The clinician's PDA automatically joins Robert's BSN in a secure manner, through key agreement, authentication and authorization according to access control policies, and receives the patient's pseudonym and $K_{BSN}$. The rest of the WMSs of the patient's BSN receive the address of the PDA from the PSMx so that they can start transmitting the patient's vital signs to the PDA in a secure manner.

The system can also implement dynamic context-aware privacy and access control policies that allow dynamic adaptation of access control rules. For instance, if a patient suffers a heart attack, the WMS can send an alarm to the PSMx, so that the PSMx can authorize any clinician to take care of the patient. Note that the mλKE still ensures secure communication in these situations, as all the WMSs in the MSN share correlated KM from the main MSN SD, and thus any pair of WMSs in the MSN can agree on a common pair-wise key.

System Performance

The performance of the disclosed security system was analyzed on resource-constrained devices, i.e., WMSs, PSM and HCC, as they represent the bottlenecks of the system. The WMS platform may include the features of MICAz as described above. It was assumed that a total of 2 Kbytes are reserved for λ-secure KM and keys of 64 bits are used. Finally, we assume that the cryptographic capabilities and performance of the HCC are similar to, e.g, the uPD789828 of NEC. Table 1 (FIG. 13) compares the performance of some security primitives on MICAz and uPD789828.

Now we can outline the efficiency of the mλKE, in accordance with the performance of several key establishment protocols for wireless sensor networks based on Blundo polynomials. The evaluation of a polynomial of order λ and a key of 64 bits requires 500·λ CPU cycles which at 8 MHz takes 0.0625·λ msec. The key distribution approach, as described above, requires the evaluation of several polynomials with a maximum size of up to 2 Kbytes, i.e., a total of 256 coefficients distributed among the different polynomials. Hence, when using 256 as λ, the polynomial evaluation time can be approximated to 16 msec. The computation of the identifiers for each of the sub-SDs of an MSN, master key, generation of a session key or the authentication handshake requires the use of a hash function. However, a hash function can be efficiently implemented using the AES hardware implementation available on the MICAz. For instance, applying the Matyas-Meyer-Oseas hash function, also used in ZigBee, a hash computation of 16 bytes takes less than 12 μsec. Therefore, the total computation time in this specific example can be approximated to 16 msec. This value indicates that this approach is much faster than public key solutions. Moreover, it has two further advantages: Firstly, a pair of WMSs only needs to exchange their MSN identifiers (2 bytes) and sub-SDs identifiers to be authenticated. This reduces the communication overhead compared with the exchange of long public keys, which helps to extend the battery lifetime of WMSs. Secondly, this approach enables the implementation of access control policies without storing long access control lists or requiring the use of digital signatures that require an expensive public key. Consequently, and assuming that a BSN comprises around 10 WMSs, the disclosed system enables secure BSN association in a time of around 160 msec. including key agreement and inherent access control, which is much faster than a single public key computation (see Table 1 (FIG. 13) for comparison) and meets the latency requirements for ECG transmission and BSN setup.

Using lightweight cryptographic primitives for frequent operations, the disclosed system frees WMSs from computationally-intensive operations and reduces the use of public key cryptography to only those security handshakes between HCC, PSM and the central healthcare trust center to configure the PSMx. These handshakes occur only sporadically in secure environments during the initial PSMx configuration. Thus, the system is not prone to DoS attacks.

Security Analysis

The multidimensional λ-secure key establishment mλKE enables fast key agreement by using decentralized key distribution approaches. However, a λ-secure key distribution system suffers from the drawback that the combination of λ independent keying material sets allows attackers to break the security of the system, i.e., to recover the original $KM^{root}$. In this section, we analyze how the disclosed multidimensional λ-secure key distribution approach not only enables distributed access control, but also optimizes the resiliency of the system, making it possible to achieve a high security level. In the following, the term resiliency, α, represents the fraction of communications that are compromised after capturing k nodes in a SD (secure domain) based on a λ-secure key distribution system. Observe that $0 \leq \alpha \leq 1$, and that α=1 when k=λ if a single polynomial is used in a SD. We denominate relative resiliency, $\alpha_r$, to the ratio between the number of compromised nodes to make α=1, i.e., λ, and the total number of WMSs, $n_{ji}$, in $SD_{ij}$. Observe that a λ-secure system with $\alpha_r$ larger than 1 is perfectly secure and that given two λ-secure SDs with equal resiliency, the one with $\alpha_r$ closer to 1 can be considered more secure as an intruder must capture the same amount of nodes from a smaller pool of WMSs. Thus resiliency is a measure of the systems's resistance to, and protection against, node compromise.

To crack the mλKE, an attacker must compromise each of the (sub-)SDs. Likewise, to break the security of the communications with a WMS, an attacker must break all of the λ-secure SDs from which the WMS has λ-secure KM. Thus, for the KM depicted in FIG. 8, an attacker must crack a total of 5 SDs to compromise the communications. Despite the fact that a single λ-secure SD, e.g., the MSN SD, is relatively easy to break because all the devices carry a set of KM from it and an attacker can acquire with a relatively small effort a small fraction of them, cracking the rest of the sub-SDs is much more difficult. This is because the relative resiliency of these SDs is higher and only some nodes in the MSN own correlated KM. Thus, if an attacker tries to remove many of the WMSs in the same (sub-)SD, it can be detected easily. Additionally, the amount of λ-secure information an attacker has to get in order to break all the communications increases as multiple λ-secure SDs are used, and even if one of them is compromised the rest remains secure.

In general, the resiliency and relative resiliency of the mλKE where a master key K is calculated as the hash of several partial keys, $K_{ji}$, generated from several λ-secure SDs, $SD_{ij}$, are given by formulas (2) and (3) respectively:

$$\alpha^{m\lambda KE} = \text{Max}\{\forall_{ji} \{n_{ji} \alpha_{ji}\}\} \quad \text{Formula (2)}$$

$$\alpha_r^{m\lambda KE} = \text{Max}\{\alpha_r^1, \ldots, \alpha_r^h, \ldots, \alpha_r^K\} \quad \text{Formula (3)}$$

Example—we assume a hospital MSN comprising a total of 1,000 WMSs (~100 patient's BSNs); two buildings, each building divided into 5 floors; and a total of 10 operational zones and 8 different medical specialties. We also assume the use of 2 Kbytes of memory to allocate λ-secure KM. Each sub-SD is assigned an amount of memory as described in Table 2 (FIG. 14) and assuming a uniform distribution of WMSs to sub-SDs, we can calculate the resiliency and relative resiliency for each sub-SD. From these values, we can conclude that an attacker must compromise 385 nodes, i.e., 38.5% of the pool of WSNs, to crack this specific system.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. A secure end-to-end patient healthcare system comprising:
    at least two wireless medical sensors adapted to be attached to a patient's body and in communication with each other forming a body sensor network within a wireless medical sensor network including one or more body sensor networks, the at least two wireless medical sensors including a first and a second wireless medical sensor;
    a memory configured to store λ-secure key material, the memory incorporated into each of said wireless medical sensors for enabling secure communications between said wireless medical sensors;
    a personal security manager within the body sensor network and in communication with said one or more wireless medical sensors within said body sensor network, said personal security manager providing secure communications with backend services and providing security relationships within said body sensor network by use of said λ-secure key material, wherein said λ-secure key material ensures that a coalition of less than λ compromised wireless medical sensors cannot calculate a pairwise key between any two non-compromised wireless medical sensors and the λ-secure key material provides protection against wireless medical sensor compromise until λ+1 wireless medical sensors have been compromised, the λ-secure key material being generated by evaluating a bivariate polynomial of degree λ; and
    a healthcare card plugged into the personal security manager, wherein the healthcare card includes identification information and security information for secure communication with the backend healthcare services, wherein the personal security manager includes a certificate issued by a local trust center, and wherein the system is adapted to execute a security protocol for auditing and/or access control and/or privacy protection, and/or mutual authentication of the personal security manager with the healthcare card wherein the first wireless medical sensor generates a pairwise key based on the λ-secure key material, encrypts a message using the pairwise key, and sends the encrypted message to the second wireless medical sensor which decrypts the message using the pairwise key.

2. A secure end-to-end patient healthcare system, comprising:
a plurality of wireless medical sensors, including a first wireless medical sensor, adapted to be attached to a patient's body and in communication with each other forming a body sensor network within a wireless medical sensor network including one or more body sensor networks, wherein information from the body sensor network is linked to the patient's identity;
a memory incorporated into each of the wireless medical sensors to store λ-secure key material which enables secure communications among said wireless medical sensors, said λ-secure key material being such that a coalition of less than λ compromised wireless medical sensors cannot calculate a pairwise key between any two non-compromised wireless medical sensors, enabling the λ-secure key material to provide protection against wireless medical system compromise until λ+1 wireless medical sensors have been compromised, said λ-secure keys being generated by evaluating a polynomial of degree λ;
a personal security manager within the body sensor network and in communication with the plurality of wireless medical sensors within said body sensor network, said personal security manager providing secure communications with backend services and using the λ-secure key material to provide security relationships within said body sensor network; and
a patient healthcare card (HCC) which plugs into the personal security manager, the healthcare card including identification information and security information for secure communication with the backend healthcare services, wherein the personal security manager includes a certificate issued by a local trust center, and wherein the system is configured to execute a security protocol for auditing and/or access control and/or privacy protection, and/or mutual authentication of the personal security manager with the healthcare card wherein said patient healthcare card (HCC) and said personal security manager (PSM) form an extended personal security manager (PSMx) for connecting a number of wireless medical sensor network security domains to a pervasive healthcare system, said extended personal security manager being configured for:
storing said certificate issued by said local trust center,
storing said λ-secure key material for establishing an end-to-end security communication issued by centralized healthcare services,
implementing said security protocol to enable mutual authentication of said extended personal security manager and said healthcare card, end-to-end security and/or auditing, and/or management of context access control and privacy policies, and
issuing λ-secure key material to the first wireless medical sensor of the plurality of wireless medical sensors, the first wireless medical sensor encrypting sensed data with the λ-secure key material and sending the encrypted sensed data to the personal security manager, the personal security manager decrypting the encrypted sensed data using the λ-secure key material.

3. The secure end-to-end patient healthcare system of claim 2, wherein said extended personal security manager is adapted for authenticating the personal security manager of the patient and patient's healthcare card when the patient joins the medical sensor network.

4. The secure end-to-end patient healthcare system of claim 2, wherein said personal security manager comprises a smart card reader adapted to receive said healthcare card, and wherein said healthcare card includes individual identification information and/or medical information and/or security material and/or security policies.

5. The secure end-to-end patient healthcare system of claim 4, wherein said personal security manager includes a user's name, identifier, security material, medical record or access control policies for different medical sensor networks.

6. The secure end-to-end patient healthcare system of claim 4, wherein said extended personal security manager includes identification of a global user, patient area network, and individual electronic healthcare information (EHI), the electronic healthcare information (EHI) coming from said patient area network.

7. The secure end-to-end patient healthcare system of claim 2, wherein security information stored on the healthcare card is provided for identifying and authenticating the user and acting as a bridge between the patient's body sensor network and centralized or backend healthcare services.

8. The secure end-to-end patient healthcare system of claim 2, wherein said extended personal security manager is a mobile phone with an additional smart card slot for the healthcare card.

9. The secure end-to-end patient healthcare system of claim 2, further comprising an autonomous secure domain formed by the wireless medical sensor associated with a body sensor network, wherein said extended personal security manager is the body sensor network's trust center and is adapted for controlling the secure association or revocation of the body sensor network's members.

10. The secure end-to-end patient healthcare system of claim 9, wherein said extended personal security manager and said wireless medical sensors are adapted for securely storing exchanged information and actions carried out in the body sensor network on the patient's healthcare card even if connectivity to the medical sensor network trust center is lost.

11. A personal security manager for a secure end-to-end patient healthcare system, wherein the personal security manager is within a body sensor network and in communication with a plurality of wireless medical sensors within said body sensor network, said personal security manager providing secure communications with backend services and providing security relationships within said body sensor network by use of λ-secure keys,
wherein the plurality of wireless medical sensors are adapted to be attached to a patient's body and in communication with each other to form said body sensor network within a wireless medical sensor network including one or more body sensor networks;
a memory storing a λ-secure key incorporated into each of said wireless medical sensors for enabling secure communications between said wireless medical sensors, the λ-secure key comprising a λ-secure keying material share provided by the personal security manager to the wireless medical sensors within the body sensor network, the wireless medical sensors encrypting sensed data with the λ-secure keying material share and sending the encrypted sensed data to the personal security manager, the personal manager decrypting the encrypted sensed data, and wherein said λ-secure keys are such that a coalition of no more than λ compromised wireless medical sensors cannot calculate a pairwise key between any two non-compromised wireless medical sensors and the λ-secure keys provide protection against node compromise until λ+1 wireless medical sensors have been compromised.

12. The secure end-to-end patient healthcare system of claim 11, wherein the λ-secure keys comprise λ-secure keying material shares derived from a polynomial of at least degree λ over a field.

13. secure end-to-end patient healthcare system of claim 12, wherein a pair of the wireless medical sensors may communicate pairwise autonomously without communication traveling through the PSM by use of the λ-secure keys stored in the memory of each wireless medical sensor.

* * * * *